US006773886B2

(12) United States Patent
Kaufman et al.

(10) Patent No.: US 6,773,886 B2
(45) Date of Patent: *Aug. 10, 2004

(54) BINARY ENCODED SEQUENCE TAGS

(75) Inventors: Joseph C. Kaufman, Hamden, CT (US); Matthew E. Roth, Branford, CT (US); Paul M. Lizardi, Wallingford, CT (US); Li Feng, Hamden, CT (US); Darin R. Latimer, East Haven, CT (US)

(73) Assignees: Yale University, New Haven, CT (US); Agilix Corporation, New Haven, CT (US)

(*) Notice: Subject to any disclaimer, the term of this patent is extended or adjusted under 35 U.S.C. 154(b) by 127 days.

This patent is subject to a terminal disclaimer.

(21) Appl. No.: 09/994,311

(22) Filed: Nov. 26, 2001

(65) Prior Publication Data

US 2003/0082556 A1 May 1, 2003

Related U.S. Application Data

(63) Continuation of application No. 09/637,751, filed on Aug. 11, 2000, now Pat. No. 6,383,754, which is a continuation-in-part of application No. 09/544,713, filed on Apr. 6, 2000, now Pat. No. 6,261,782.
(60) Provisional application No. 60/148,870, filed on Aug. 13, 1999.

(51) Int. Cl.[7] .............................. C12Q 1/68; C12P 19/34
(52) U.S. Cl. ....................... 435/6; 435/91.1; 435/91.2; 436/94
(58) Field of Search ....................... 435/6, 91.1, 91.2; 436/94

(56) References Cited

U.S. PATENT DOCUMENTS

| 5,429,807 A | 7/1995 | Matson et al. |
| 5,508,169 A | 4/1996 | Deugau et al. |
| 5,599,675 A | 2/1997 | Brenner |
| 5,599,695 A | 2/1997 | Pease et al. |
| 5,607,924 A | 3/1997 | Magda et al. |
| 5,654,413 A | 8/1997 | Brenner |
| 5,707,807 A * | 1/1998 | Kato ............................ 435/6 |
| 5,710,000 A | 1/1998 | Sapolsky et al. |
| 5,728,524 A | 3/1998 | Sibson |
| 5,736,330 A | 4/1998 | Fulton |
| 5,854,033 A | 12/1998 | Lizardi |
| 5,858,656 A | 1/1999 | Deugau et al. |
| 5,858,671 A | 1/1999 | Jones |
| 5,871,697 A | 2/1999 | Rothberg et al. |
| 5,871,918 A | 2/1999 | Thorp et al. |
| 5,871,928 A | 2/1999 | Fodor et al. |
| 5,968,745 A | 10/1999 | Thorp et al. |
| 5,985,153 A | 11/1999 | Dolan et al. |
| 5,993,665 A | 11/1999 | Terstappen et al. |
| 5,994,068 A | 11/1999 | Guilfoyle et al. |
| 6,013,188 A | 1/2000 | Terstappen et al. |
| 6,023,540 A | 2/2000 | Walt et al. |
| 6,027,894 A | 2/2000 | Sapolsky et al. |
| 6,232,067 B1 | 5/2001 | Hunkapiller et al. ............ 435/6 |
| 6,258,539 B1 | 7/2001 | Hunkapiller et al. ............ 435/6 |
| 6,261,782 B1 | 7/2001 | Lizardi et al. |
| 6,403,319 B1 | 6/2002 | Lizardi et al. |

FOREIGN PATENT DOCUMENTS

| WO | WO 97/19193 A2 | 5/1997 |
| WO | WO 98/50782 A2 | 5/1998 |
| WO | WO 99/19515 A1 | 4/1999 |
| WO | WO 99/28505 A1 | 6/1999 |
| WO | WO 99/37814 A1 | 7/1999 |
| WO | WO 99/64847 A1 | 12/1999 |
| WO | WO 00/04036 A1 | 1/2000 |
| WO | WO 00/08843 A1 | 2/2000 |

OTHER PUBLICATIONS

Adams, et al., "Complementary DNA sequencing: expressed sequence tags and human genome project," *Science* 252(5013):1651–56 (1991).
Adams, et al., "Initial assessment of human gene diversity and expression patterns based upon 83 million nucleotides of cDNA sequence," *Nature* 377:3–174 (1995).
Airoldi, et al., "Carcinogen–DNA adducts as tools in risk assessment," *Adv. Exp. Med. Biol.* 472:231–40 (1999).
Alwine, et al., "Method for detection of specific RNAs in agarose gels by transfer to diazobenzyloxymethyl–paper and hybridization with DNA probes," *Proc. Natl. Acad. Sci. U. S. A.* 74(12):5350–4 (1977).
Bauer, et al., "Identification of differentially expressed mRNA species by an improved display technique (DDRT–PCR)," *Nucleic Acids Res.* 21(18):4272–80 (1993).

(List continued on next page.)

*Primary Examiner*—Kenneth R. Horlick
(74) *Attorney, Agent, or Firm*—Needle & Rosenberg, P.C.

(57) ABSTRACT

Disclosed is a method for the comprehensive analysis of nucleic acid samples and a detector composition for use in the method. The method, referred to as Binary Encoded Sequence Tags (BEST), involves generation of a set of nucleic acid fragments; adding an adaptor to the ends containing recognition site for cleavage at a site offset from the recognition site; cleaving the fragment to generate fragments having a plurality sticky ends; indexing of the fragments into sets based on the sequence of sticky ends. The fragments are indexed by adding a offset adaptor to newly generated ends. A different adaptor will be coupled to each different sticky end. The resulting fragments—which will have defined ends, be of equal lengths (in preferred embodiment), and a central sequence derived from the source nucleic acid molecule—are binary sequence tags. The binary sequence tags can be used and further analyzed in numerous ways. For example, the binary sequence tags can be captured by hybridization and coupling, preferably by ligation, to a probe. The probe is preferably immobilized in an array or on sortable beads. One form of the BEST method, referred to as modification assisted analysis of binary sequence tags (MAABST), assesses modification of sequences in nucleic acid molecules by detecting differential cleavage based on the presence or absence of modification in the molecules.

15 Claims, 3 Drawing Sheets

OTHER PUBLICATIONS

Baylin, et al., "Alterations in DNA methylation: a fundamental aspect of neoplasia," *Adv. Cancer Res.* 72: 141–96 (1998).

Bird & Wolffe, "Methylation–induced repression—belts, braces, and chromatin," *Cell* 99(5):451–4 (1999).

Bird, "DNA methylation de novo," *Science* 286(5448):2287–8 (1999).

Birkenmeyer & Mushahwar, "DNA probe amplification methods," *J. Virol. Methods* 35(2):117–26 (1991).

Breaker & Joyce, "A DNA enzyme that cleaves RNA," *Chemistry & Biology* 1:223–229 (1994).

Breslauer, et al., "Predicting DNA duplex stability from the base sequence," *Proc. Natl. Acad. Sci. U. S. A.* 83(11):3746–50 (1986).

Carmi, et al., "Cleaving DNA with DNA," *Proc. Natl. Acad. Sci. U. S. A.* 95(5):2233–7 (1998).

Cartwright, et al., "Cleavage of chromatin with methidium-propyl–EDTA . iron(II)," *Proc. Natl. Acad. Sci. U. S. A.* 80(11):3213–7 (1983).

Chan & Nie, "Quantum dot bioconjugates for ultrasensitive nonisotopic detection," *Science* 281–2016–18 (1998).

Chee, et al., "Accessing genetic information with high–density DNA arrays," *Science* 274(5287):610–4 (1996).

Costello, et al., "Aberrant CpG–island methylation has non–random and tumour–type–specific patterns," *Nat. Genet.* 24(2):132–8 (2000).

Davis & Bjorkman, "T–cell antigen receptor genes and T–cell recognition," *Nature* 334:395–402 (1988).

Dayhoff, et al., "A model of evolutionary changes in proteins" in *Atlas of Protein Sequence and Structure,* M.O. Dayhoff, Editor. 1978, National Biomedical Research Foundation: Washington DC.

De Haas, et al., "Platinum porphyrins as phosphorescent label for time microscopy," *J. Histochem. Cytochem.* 45(9):1279–92 (1997).

Diatchenko, et al., "Suppression subtractive hybridization: a method for generating differentially regulated or tissue–specific cDNA probes and libraries," *Proc. Natl. Acad. Sci. U. S. A.* 93(12):6025–30 (1996).

Edman, et al., "Identification of ErbB3–stimulated genes using modified representational difference analysis," *Biochem. J.* 323 (Pt 1):113–8 (1997).

Ellis, et al., "Chemical cleavage of mismatch: a new look at an established method," *Hum. Mutat.* 11(5):345–53 (1998).

Finnegan, et al., "DNA Methylation in Plants," *Annual Rev. Physiol.* 49:223–247 (1998).

Fodor, et al., "Multiplexed biochemical assays with biological chips," *Nature* 364:555–556 (1993).

Freier, et al., "Improved free–energy parameters for predictions of RNA duplex stability," *Proc. Natl. Acad. Sci. U. S. A.* 83(24):9373–7 (1986).

Gamboa Da Costa, et al., "Characterization of the Major DNA Adduct Formed by alpha–Hydroxy-N-desmethyltamoxifen in Vitro and in Vivo," *Chem. Res. Toxicol.* 13(3):200–207 (2000).

Gonzalgo & Jones, "Rapid quantitation of methylation differences at specific sites using methylation–sensitive single nucleotide primer extension (Ms–SNuPE)," *Nucl. Acids Res.* 25:2529–31 (1997).

Guo, et al., "Direct fluorescence analysis of genetic polymorphisms by hybridization with oligonucleotide arrays on glass supports," *Nucleic Acids Res.* 22(24):5456–5465 (1994).

Habraken, et al., "ATP–dependent assembly of a ternary complex consisting of a DNA mismatch and the yeast MSH2–MSH6 and MLH1–PMS1 protein complexes," *J. Biol. Chem.* 273(16):9837–41 (1998).

Habraken, et al., "Binding of insertion/deletion DNA mismatches by the heterodimer of yeast mismatch repair proteins MSH2 and MSH3," *Curr. Biol.* 6(9):1185–7 (1996).

Hanvey, et al., "Antisense and antigene properties of peptide nucleic acids," *Science* 258(5087):1481–5 (1992).

Hatada, et al., "A genomic scanning method for higher organisms using restriction sites as landmarks," *Proc. Natl. Acad. Sci. USA* 88:9523–27 (1991).

Hedrick, et al., "Isolation of cDNA clones encoding T cell–specific membrane–associated proteins," *Nature.* 308(5955):149–53 (1984).

Hermanson, et al., *Immobilized Affinity Ligands.* (Academic Press, New York, 1992).

Hoheisel, "Sequence–independent and linear variation of oligonucleotid DNA binding stabilities," *Nucleic Acids Res.* 24(30):430–2 (1996).

Hoy, et al., "Bromodeoxyuridine/DNA analysis of replication in CHO cells after exposure to UV light," *Mutat. Res.* 290(2):217–30 (1993).

Hsu, "Mismatch cleavage detects base deletion in cystic fibrosis gene," *Biotechniques* 25:692–6 (1998)

Hubank & Schatz, "Identifying differences in mRNA expression by representational difference analysis of cDNA," *Nucleic Acids Res.* 22:5640–8 (1994).

Ito & Sakaki, "Fluorescent differential display," *Methods Mol. Biol.* 85:37–44 (1997).

Johnstone & Thorpe, *Immunochemistry In Practice* (Blackwell Scientific Publications, Oxford, England, 1987) pp. 209–216 and 241–242.

Karger, et al., "Digital chemiluminescence imaging of DNA sequencing blots using a charge–coupled device camera," *Nucleic Acids Res.* 20(24):6657–65 (1992).

Kerkhof, "A Comparison of Substrates for Quantifying the Signal from a Nonradiolabeled DNA Probe," *Analytical Biochemistry* 205:359–364 (1992).

Keyes, et al., "Overall and internal dynamics of DNA as monitored by five–atom–tethered spin labels," *Biophys. J.* 72(1):282–90 (1997).

Khrapko, et al., "Hybridization of DNA with oligonucleotides immobilized in a gel: a convenient method for recording single base replacements," *Mol. Biol. (Mosk).* 25(3):718–30 (1991).

Kirschstein, et al., "Detection of the DeltaF508 mutation in the CFTR gene by means of time–resolved fluorescence methods," *Bioelectrochem. Bioenerg.* 48(2):415–21 (1999).

Kortenkamp, et al., "Genotypic selection of mutated DNA sequences using mismatch cleavage analysis, a possible basis for novel mutation assays," *Mutagenesis* 12:335–8 (1997).

Kozian & Kirschbaum, "Comparative gene–expression analysis," *Trends Biotechnol.* 17(2):73–8 (1999).

Kricka, "Chemiluminescent and bioluminescent techniques," *Clin. Chem.* 37(9):1472–81 (1991).

Kricka, "Selected strategies for improving sensitivity and reliability of immunoassays," *Clin. Chem.* 40(3):347–57 (1994).

Kumke, et al., "Temperature and quenching studies of fluorescence polarization detection of DNA hybridization," *Anal. Chem.* 69(3):500–6 (1997).

Landegren, "Molecular mechanics of nucleic acid sequence amplification," *Trends Genetics* 9:199–202 (1993).

Langer, et al., "Enzymatic synthesis of biotin–labeled polynucleotides: Novel nucleic acid affinity probes," *Proc. Natl. Acad. Sci. USA* 78(11):6633–6637 (1981).

Lavery, et al., "Selective Amplification via biotin– and restriction –mediated enrichment (SABRE), a novel selective amplification procedure for detection of differentially expressed mRNAs," *Proc. Natl. Acad. Sci. U. S. A.* 94(13):6831–6 (1997).

Lee, et al., "Comparative expressed–sequence–tag analysis of differential gene expression profiles in PC–12 cells before and after nerve growth factor treatment," *Proc. Natl. Acad. Sci. U. S. A.* 92(18):8303–7 (1995).

Liang & Pardee, "Differential display of eukaryotic messenger RNA by means of the polymerase chain reaction," *Science.* 57(5072):967–71 (1992).

Liang & Pardee, "Recent Advances in differential display," *Curr. Opin. Immunol.* 7(2):274–80 (1995).

Lipshutz, "Likelihood DNA sequencing by hybridization," *J. Biomol. Struct. Dyn.* 11(3):637–53 (1993).

Lisitsyn, et al., "Cloning the differences between two complex genomes." *Science* 259(5097):946–51 (1993).

Lizardi, et al., "Mutation detection and single–molecule counting using isothermal rolling–circle amplification," *Nat Genet.* 19(3):225–32 (1998).

Lodovici, et al., "Levels of 8–hydroxydeoxyguanosine as a marker of DNA damage in human leukocytes," *Free Radic. Biol. Med.* 28(1):13–7 (2000).

Lu & Hsu, "Detection of single DNA base mutations with mismatch repair enzymes," *Genomics* 14(2):249–55 (1992).

Maehira, et al., "Alterations of protein kinase C, 8–hydroxydeoxyguanosine, and K–ras oncogene in rat lungs exposed to passive smoking," *Clin. Chim. Acta.* 298(1–2):133–44 (1999).

Maniatis, et al., "The isolation of structural genes from libraries of eucaryotic DNA," *Cell* 15(2):687–701 (1978).

Mansfield, et al., "Nucleic acid detection using non–radioactive labeling methods," *Mol. Cell Probes* 9(3):145–56 (1995).

Mashal, "Detection of mutations by cleavage of DNA heteroduplexes with bacteriophage resolvases," *Nat. Genet.* 9:177–83 (1995).

McCreery, "Digoxigenin labeling," *Mol. Biotechnol.* 7(2):121–4 (1997).

Melki, et al., "Concurrent DNA hypermethylation of multiple genes in acute myeloid leukemia," *Cancer Res.* 59(15):3730–40 (1999).

Michael, et al., "Randomly ordered addressable high–density optical sensor arrays," *Anal. Chem..* 70(7):1242–8 (1998).

Napier, et al., "Probing biomolecule recognition with electron transfer: electrochemical sensors for DNA hybridization," *Bioconjug. Chem.* 8(6):906–13 (1997).

Neddermann & Jiricny, "Efficient removal of uracil from G.U mispairs by the mismatch–specific thymine DNA glycosylase from HeLa cells," *Proc. Natl. Acad. Sci. U. S. A.* 91(5):1642–6 (1994).

Nguyen, et al., "Modification of DNA duplexes to smooth their thermal stability independently of their base content for DNA sequencing by hybridization," *Nucleic Acids Res.* 25(15):3059–3065 (1997).

Nguyen, et al., "Smoothing of the thermal stability of DNA duplexes by using modified nucleosides and chaotropic agents," *Nucleic Acids Res.* 27(6):1492–1498 (1999).

Nikiforov, et al., "Genetic Bit Analysis: a solid phase method for typing single nucleotide polymorphisms," *Nucleic Acids Res.* 22(20):4167–75 (1994).

Nikiforov, et al., "The Use of Phosphorothioate Primers and Exonuclease Hydrolysis for the Preparation of Single––Standed PCR Products and their Detection by Solid–phase Hybridization," *PCR Methods and Applications* 3:285–291 (1994).

Nurmi, et al., "A new label technology for the detection of specific polymerase chain reaction products in a closed tube," *Nucleic Acids Res.* 28(8):28 (2000).

O'Neill & Sinclair, "Isolation of rare transcripts by representational difference analysis," *Nucleic Acids Res.* 25:2681–2682 (1997).

Oetting, et al., "Multiplexed short tandem repeat polymorphisms of the Weber 8A set of markers using tailed primers and infrared fluorescence detection," *Electrophoresis* 19(18):3079–83(1998).

Olejnik, et al., "Photocleavable affinity tags for isolation and detection of biomolecules," *Methods Enzymol.* 291:135–54 (1998).

Olejnik, et al., "Photocleavable aminotag phosphoramidites for 5'–termini DNA/RNA labeling," *Nucleic Acids Res.* 26(15):3572–6 (1998).

Olejnik, et al., "Photocleavable biotin derivatives: a versatile approach for the isolation of biomolecules," *Proc. Natl. Acad. Sci. U. S. A.* 92(16):7590–4 (1995).

Olejnik, et al., "Photocleavable biotin phosphoramidite for 5'–end–labeling, affinity purification and phosphorylation of synthetic oligonucleotides," *Nucleic Acids Res.* 24:361–66 (1996).

Olejnik, et al., "Photocleavable peptide–DNA conjugates: synthesis and applications to DNA analysis using MALDI–MS," *Nucleic Acids Res.* 27(23):4626–31 (1999).

Paciotti, et al., "Mec 1p is essential for phosphorylation of the yeast DNA damage checkpoint protein Dcd1p, which physically interacts with Mec3p," *EMBO J.* 17(14):4199–209 (1998).

Pang, et al., "Functional domains of the *Saccharomyces cerevisiae* Mlh1p and Pms1 p DNA mismatch repair proteins and their relevance to human hereditary nonpolyposis colorectal cancer–associated mutations," *Mol. Cell. Biol.* 17(8):4465–73 (1997).

Pease, et al., "Light–generated oligonucleotide arrays for rapid DNA sequence analysis," *Proc. Natl. Acad. Sci. USA* 91(11):5022–5026 (1994).

Phillips, et al., "Methods of DNA adduct determination and their application to testing compounds for genotoxicity," *Environ. Mol. Mutagen* 35(3):222–233 (2000).

Podhajska & Szybalski, "Conversion of the Fokl endonuclease to a universal restriction enzyme: cleavage of phage M13mp7 DNA at predetermined sites," *Gene* 40(2–3):175–82 (1985) [published erraatum appears in gene 43(3):3254 (1985))].

Prashar & Weissman, "Analysis of differential gene expression by display of 3' end restriction fragments of cDNAs," *Proc. Nat. Acad. Sci. U.S.A.* 93:659–663 (1996).

Purewal, et al., "Association between acetylator genotype and 2–amino–1–methyl–6–phenylimidazol[4,5–b]pyridine (PhIP) DNA adduct formation in colon and prostate of inbred Fischer 344 and Wistar Kyoto rats," *Cancer Lett.* 149(1–2):53–60 (2000).

Rabinowicz, et al., "Differential methylation of genes and retrotransposons facilitates shotgun sequencing of the maize genome," *Nat. Genet.* 23:305–308 (1999).

Ren, et al., "Chemical mismatch cleavage combined with capillary electrophoresis: detection of mutations exon 8 of the cystathionine beta–synthase gene," *Clin. Chem.* 44:2108–14 (1998).

Roda, et al., "Chemiluminescent imaging of enzyme–labeled probes using an optical microscope–videocamera luminograph," *Anal. Biochem.* 257(1):53–62 (1998).

Santalucia, et al., "Improved nearest–neighbor parameters for predicting DNA duplex stability," *Biochemistry* 35:3555–3562 (1996).

Schena, et al., "Quantitative Monitoring of Gene Expression Patterns with a Complementary DNA Microarray," *Science* 270:467–470 (1995).

Schultz & Dervan, "Sequence–specific double–strand cleavage of DNA by penta–N– methylpyrrolecarboxamide–EDTA X Fe(II)," *Proc. Natl. Acad. Sci. U. S. A.* 80(22):6837–7 (1983).

Sewell & Durbin, "Method for calculation of Probability of matching a bounded regular expression in a random data string," *J. of Computational Biology* 2:25–31 (1995).

Siddiqi, et al., "Evaluation of electrochemiluminescence––and bioluminescence–based assays for quantitating specific DNA," *J. Clin. Lab. Anal.* 10(6):423–31 (1996).

Squire, et al., "Multiple frequency fluorescence lifetime imaging microscopy," *J. Microscopy* 197(2):136–149 (2000).

Stevenson, et al., "Synchronous luminescence: a new detection technique for multiple flourescent probes used for DNA sequencing," *Biotechniques* 16(6):1104–11 (1994).

Stimpson, et al., "Real–time detection of DNA hybridization and melting on oligonucleotide arrays by using optical wave guides," *Proc. Natl. Acad. Sci. USA* 92(14):6379–6383 (1995).

Swaroop, et al., "A simple and efficient cDNA library subtraction procedure: isolation of human retina–specific cDNA clones," *Nucleic Acids Res.* 19(8):1954 (1991).

Syvänen, et al., "Fast quantification of nucleic acid hybrids by affinity–based hybrid collection," *Nucleic Acids Res.* 14(12):5037–48 (1986).

Szybalski, "Universal restriction endonucleases: designing novel cleavage specificities by combining adapter oligodeoxynucleotide and enzyme moieties," *Gene* 40(2–3):169–73 (1985).

Taylor, *Protein immobilization: fundamentals and applications* (M. Dekker, New York, 1991).

Tibbe, et al., "Optical tracking and detection of immunomagnetically selected and aligned cells," *Nat. Biotechnol.* 17(12):1210–3 (1999).

Unrau & Deugau, "Non–cloning amplification of specific DNA fragments from whole genomic DNA digests using DNA 'indexers'" *Gene* 145:163–169 (1994).

Vasmatzis, et al., "Discovery of three genes specifically expressed in human prostate by expressed sequence tag database analysis," *Proc. Natl. Acad. Sci. U. S. A.* 95:300–304 (1998).

Velculescu, et al., "Serial analysis of gene expression," *Science.* 270(5235):484–7 (1995).

Venezia & O'Hara, "Rapid motif compliance scoring with match weight sets," *Comput. Appl. Biosci.* 9(1):65–9 (1993).

Vo–Dinh, et al., "Surface–enhanced Raman gene probes," *Anal. Chem.* 66(20):3379–83 (1994).

Volkers, et al., "Microwave label detection technique for DNA in situ hybridization," *Eur. J. Morphol.* 29(1):59–62 (1991).

Wada, et al., "Representational difference of cDNA of genes expressed in embryonic kidney," *Kidney Int.* 51:1629–1638 (1997).

Walker, et al., "Strand displacement amplification—an isothermal, in vitro DNA amplification technique," *Nucleic Acids Res.* 20(7):1691–6 (1992).

Walt, "Techview: molecular biology. Bead–based fiber–optic arrays," *Science* 287(5452):451–2 (2000).

Wansink, et al., "Fluorescent Labeling of Nascent RNA Reveals Transcription by RNA Polymerase II in Domains Scattered Throughout the Nucleus," *Journal of Cell Biology* 122(2):283–293 (1993).

Whitney, et al., "A genome–wide functional assay of signal transduction in living mammalian cells," *Nat. Biotechnol.* 16(13):1329–33 (1998).

Wood, et al., "Base composition–independent hybridization in tetramethylammonium chloride: a method for oligonucleotide screening of highly complex gene libraries," *Proc. Natl. Acad. Sci. USA* 82(6):1585–1588 (1985).

Xiong & Laird, "COBRA: a sensitive and quantitative DNA methylation assay," *Nuc. Acid Res.* 25(12):2532–2534 (1997).

Yao & Kow, "Further characterization of *Escherichia coli* endonuclease V. Mechanism of recognition for deoyinosine, deoxyuridine, and base mismatches in DNA," *J. Biol. Chem.* 272:30774–79 (1997).

Yeh, et al., "Mammalian topoisomerase 1 has base mismatch nicking activity," *J. Biol. Chem.* 269(22):15498–504 (1994).

Youil, et al., "Detection of 81 of 81 known mouse beta––globin promoter mutations with T4 endonuclease VII—the EMC method," *Genomics* 32:431–435 (1996).

Yu, et al., "Cyanine dye dUTP analogs for enzymatic labeling of DNA probes," *Nucleic Acids Research* 22(15):3226–3232 (1994).

Zlokarnik, et al., "Quantitation of transcription and clonal selection of single living cells with β–lactamase as reporter," *Science* 279:84–88 (1998).

* cited by examiner

FIG. 1A

| | Adaptor-indexer I | Adaptor-indexer II |
|---|---|---|
| | CATGCGGATCCTAAGGCTTACGCC | TAATGGAAGCTGGATTCCGCG |
| | GCCTAGGATTCCGAATGCGG | GTTCATTACCTTCGACCTAAGCGC |
| | Ligator-detectors | Ligator-detectors |
| 1. | CATGCGGATCCTAAGGCTTACGCC | |
| 2. | CATGCGGATCCTAAGGCTTACGC | |
| 3. | CATGCGGATCCTAAGGCTTA | |
| 4. | CATGCGGATCCTAAGGC | |
| 5. | ATGCGGATCCTAAGGCTTACGCC | |
| 6. | TGCGGATCCTAAGGCTTACGCC | |
| 7. | GCGGATCCTAAGGCTTACGCC | |
| 21. | CAAGTAATGGAAGCTGGATTCCGCG | |
| 22. | CAAGTAATGGAAGCTGGATTCGC | |
| 23. | CAAGTAATGGAAGCTGGATTC | |
| 24. | CAAGTAATGGAAGCT | |
| 25. | AAGTAATGGAAGCTGGATTCCGCG | |
| 26. | AGTAATGGAAGCTGGATTCCGCG | |
| 27. | GTAATGGAAGCTGGATTCCGCG | |

FIG. 1B

8.  ATGCGGGATCCCTAAGGCTTACGC AAGTAATGGAAGCTGGATTCGC
9.  ATGCGGGATCCCTAAGGCTTACG AAGTAATGGAAGCTGGATTC
10. ATGCGGGATCCCTAAGGCTT AAGTAATGGAAGCTGGAT
11. ATGCGGGATCCCTAAGGC AAGTAATGGAAGCTG
12. TGCGGGATCCCTAAGGCTTAC AGTAATGGAAGCTGGATTCGCG
13. GGCGTAAGCCTTAGGATCCGCATC CGCGAATCCAGCTTCCATTACTTG
14. GCCGTAAGCCTTAGGATCCGCATC GCGAATCCAGCTTCCATTACTTG
15. GTAAGCCTTAGGATCCGCATC GAATCCAGCTTCCATTACTTG
16. CCTTAGGATCCGCAT CAGCTTCCATTACTTG
17. GGCGTAAGCCTTAGGATCCGCAT CGCGAATCCAGCTTCCATTACTT

FIG. 1C

18. GGCGTAAGCCTTAGGATCCGCA
19. GGCGTAAGCCTTAGGATCCGC
20. GCATGCGGATCCTAAGGCTTACGCC

38. CGCGAATCCAGCTTCCATTACT
39. CGCGAATCCAGCTTCCATTAC
40. GAATCCAGCTTCCATTACTT

BINARY ENCODED SEQUENCE TAGS

CROSS-REFERENCE TO RELATED APPLICATIONS

This application is a continuation of U.S. application Ser. No. 09/637,751, filed Aug. 11, 2000, U.S. Pat. No. 6,383,754, which application is a continuation-in-part of U.S. application Ser. No. 09/544,713, filed Apr. 6, 2000, U.S. Pat. No. 6,261,782, which claims the benefit of U.S. Provisional Application No. 60/148,870, filed Aug. 13, 1999, by Paul M. Lizardi and Darin R. Latimer, entitled "Analysis of Sequence Tags With Hairpin Primers", which applications are hereby incorporated herein in their entirety by reference.

BACKGROUND OF THE INVENTION

The disclosed invention is generally in the field of nucleic acid characterization and analysis, and specifically in the area of analysis and comparison of gene expression patterns, nucleic acid samples, and genomes.

The study of differences in gene-expression patterns is one of the most promising approaches for understanding mechanisms of differentiation and development. In addition, the identification of disease-related target molecules opens new avenues for rational pharmaceutical intervention. Currently, there are two main approaches to the analysis of molecular expression patterns: (1) the generation of mRNA-expression maps and (2) examination of the 'proteome', in which the expression profile of proteins is analyzed by techniques such as two-dimensional gel electrophoresis, mass spectrometry [matrix-assisted-desorption-ionization-time-of-flight (MALDI-TOF) or electrospray] and by the ability to sequence sub-picomole amounts of protein. Classical approaches to transcript imaging, such as northern blotting or plaque hybridization, are time-consuming and material-intensive methods to analyze mRNA-expression patterns. For these reasons, other methods for high-throughput screening in industrial and clinical research have been developed.

A breakthrough in the analysis of gene expression was the development of the northern-blot technique in 1977 (Alwine et al., *Proc. Natl. Acad. Sci. U.S.A.* 74:5350–5354 (1977)). With this technique, labeled cDNA or RNA probes are hybridized to RNA blots to study the expression patterns of mRNA transcripts. Alternatively, RNase-protection assays can detect the expression of specific RNAs. These assays allow the expression of mRNA subsets to be determined in a parallel manner. For RNase-protection assays, the sequence of the analyzed mRNA has to be known in order to synthesize a labeled cDNA that forms a hybrid with the selected mRNA; such hybrids resist RNA degradation by a single-strand-specific nuclease and can be detected by gel electrophoresis. As a third approach, differential plaque-filter hybridization allows the identification of specific differences in the expression of cloned cDNAs (Maniatis et al. *Cell* 15:687–701 (1978)). Although all of these techniques are excellent tools for studying differences in gene expression, the limiting factor of these classical methods is that expression patterns can be analyzed only for known genes.

The analysis of gene-expression patterns made a significant advance with the development of subtractive cDNA libraries, which are generated by hybridizing an mRNA pool of one origin to an mRNA pool of a different origin. Transcripts that do not find a complementary strand in the hybridization step are then used for the construction of a cDNA library (Hedrick et al., *Nature* 308:149–153 (1984)). A variety of refinements to this method have been developed to identify specific mRNAs (Swaroop et al., *Nucleic Acids Res.* 25:1954 (1991); Diatchenko et al, *Proc. Natl. Acad. Sci. U.S.A* 93:6025–6030 (1996)). One of these is the selective amplification of differentially expressed mRNAs via biotin- and restriction-mediated enrichment (SABRE; Lavery et al., *Proc. Natl Acad. Sci. U.S.A.* 94:6831–6836 (1997)), cDNAs derived from a tester population are hybridized against the cDNAs of a driver (control) population. After a purification step specific for tester-cDNA-containing hybrids, tester—tester homohybrids are specifically amplified using an added linker, thus allowing the isolation of previously unknown genes.

The technique of differential display of eukaryotic mRNA was the first one-tube method to analyze and compare transcribed genes systematically in a bi-directional fashion; subtractive and differential hybridization techniques have only been adapted for the unidirectional identification of differentially expressed genes (Liang and Pardee, *Science* 257:967–971 (1992)). Refinements have been proposed to strengthen reproducibility, efficiency, and performance of differential display (Bauer et al., *Nucleic Acids Res.* 11:4272–4280 (1993); Liang and Pardee, *Curr. Opin. Immunol.* 7:274–280 (1995); Ito and Sakaki, *Methods Mol. Biol.* 85:37–44 (1997); Praschar and Weissman, *Proc. Natl. Acad. Sci U.S.A.* 93;659–663 (1996), Shimkets et al., *Nat Biotechnol,* 17:798–803 (1999)). Although these approaches are more reproducible and precise than traditional PCR-based differential display, they still require the use of gel electrophoresis. This often implies the exclusion of certain DNA fragments from analysis.

Originally developed to identify differences between two complex genomes, representational difference analysis (RDA) was adapted to analyze differential gene expression by taking advantage of both subtractive hybridization and PCR (Lisitsyn et al., *Science* 259:946–951 (1993); Hubank and Schatz, *Nucleic Acids Res.* 22:5640–5648 (1994)). In the first step, mRNA derived from two different populations, the tester and the driver (control), is reverse transcribed; the tester cDNA represents the cDNA population in which differential gene expression is expected to occur. Following digestion with a frequently cutting restriction endonuclease, linkers are ligated to both ends of the cDNA. A PCR step then generates the initial representation of the different gene pools. The linkers of the tester and driver cDNA are digested and a new linker is ligated to the ends of the tester cDNA. The tester and driver cDNAs are then mixed in a 1:100 ratio with an excess of driver cDNA in order to promote hybridization between single-stranded cDNAs common in both tester and driver cDNA pools. Following hybridization of the cDNAs, a PCR exponentially amplifies only those homoduplexes generated by the tester cDNA, via the priming sites on both ends of the double-stranded cDNA (O'Neill and Sinclair, *Nucleic Acids Res.* 25:2681–2682 (1997); Wada et al., *Kidney Int.* 51:1629–1638 (1997); Edman et al., *J.* 323:113–118 (1997)).

The gene-expression pattern of a cell or organism determines its basic biological characteristics. In order to accelerate the discovery and characterization of mRNA-encoding sequences, the idea emerged to sequence fragments of cDNA randomly, direct from a variety of tissues (Adams et al., *Science* 252:1651–1656 (1991); Adams et al., *Nature* 377:3–16 (1995)). These expressed sequence tags (ESTs) allow the identification of coding regions in genome-derived sequences. Publicly available EST databases allow the comparative analysis of gene expression by computer. Differentially expressed genes can be identified by comparing the databases of expressed sequence tags of a given organ or cell type with sequence information from a different origin (Lee et al., *Proc. Natl. Acad. Sci. U.S.A.* 92:8303–8307 (1995); Vasmatzis et al., *Proc. Natl. Acad. Sci. U.S.A.* 95:300–304 (1998)). A drawback to sequencing of ESTs is the requirement for large-scale sequencing facilities.

Serial analysis of gene expression (SAGE) is a sequence-based approach to the identification of differentially expressed genes through comparative analyses (Velculescu et al., *Science* 270:484–487 (1995)). It allows the simultaneous analysis of sequences that derive from different cell population or tissues. Three steps form the molecular basis for SAGE: (1) generation of a sequence tag (10–14 bp) to identify expressed transcripts; (2) ligation of sequence tags to obtain concatemers that can be cloned and sequenced; and (3) comparison of the sequence data to determine differences in expression of genes that have been identified by the tags. This procedure is performed for every mRNA population to be analyzed. A major drawback of SAGE is the fact that corresponding genes can be identified only for those tags that are deposited in gene banks, thus making the efficiency of SAGE dependent on the extent of available databases. Alternatively, a major sequencing effort is required to complete a SAGE data set capable of providing 95% coverage of any given mRNA population, simply because most of the sequencing work yields repetitive reads on those tags that are present at high frequency in cellular mRNA. In other words, SAGE sequencing experiments yield diminishing returns for rare mRNAs, whose unique tags will begin to accumulate in the database only after many weeks of sequencing effort.

A different approach to the study of gene-expression profiles and genome composition is the use of DNA microarrays. Current DNA microarrays are systematically gridded at high density. Such microarrays are generated by using cDNAs (for example, ESTs), PCR products or cloned DNA, which are linked to the surface of nylon filters, glass slides or silicon chips (Schena et al., *Science* 270, 467–470 (1995)). DNA arrays can also be assembled from synthetic oligonucleotides, either by directly applying the synthesized oligonucleotides to the matrix or by a more sophisticated method that combines photolithography and solid-phase chemical synthesis (Fodor et al., *Nature* 364:555–556 (1993)). To determine differences in gene-expression, labeled cDNAs or oligonucleotides are hybridized to the DNA- or oligomer-carrying arrays. When using different fluorophores for labeling cDNAs or oligonucleotides, two probes can be applied simultaneously to the array and compared at different wavelengths. The expression of 10,000 genes and more can be analyzed on a single chip (Chee et al., *Science* 274:610–614 (1996)). However, depending on the sensitivity of both cDNA and oligonucleotide arrays, the intensity of hybridization signals can leave the linear range when either weakly or abundantly expressed genes are analyzed. Thus, individual optimization steps are required to ensure the accurate detection of differentially expressed genes. While such microarray methods may be used to address a number of interesting biological questions, they are not suitable for the discovery of new genes.

Techniques of tagging DNA fragments using sticky end-specific adaptors have been described by Burger and Schinzel, *Mol Gen Genet.* 189:269–274 (1983), Mandecki and Bolling, *Gene,* 68:101–107 (1988), Posfai and Szybalski, *Gene,* 74:179–181 (1988), Urlaub et al., *Proc. Natl. Acad. Sci.,* 82:1189–1193 (1985), Vermesch and Bennett, *Gene,* 54:229–238 (1987), Unrau and Deugau, *Gene,* 145(2):163–9 (1994)). These techniques all involve the use of existing restriction sites and produce tagged fragments of various lengths.

There is a need for a method that combines the power and convenience of array hybridization technology with the capability for gene discovery inherent in differential display or SAGE. Such a method would be most attractive if it could enable comprehensive gene expression analysis without the use of gel electrophoresis, and without the need for a redundant DNA sequencing effort.

Therefore, it is an object of the present invention to provide a method for the comprehensive analysis of nucleic acid sequence tags.

It is another object of the present invention to provide a detector composition that allows indexing of nucleic acid sequence tags.

It is another object of the present invention to provide catalogs of sequence tags from nucleic acid samples.

BRIEF SUMMARY OF THE INVENTION

Disclosed is a method for the comprehensive analysis of nucleic acid samples and a detector composition for use in the method. The method, referred to as Binary Encoded Sequence Tags (BEST), involves generation of a set of nucleic acid fragments; adding an adaptor to the ends containing a recognition site for cleavage at a site offset from the recognition site; cleaving the fragment to generate fragments having a plurality of sticky ends; indexing of the fragments into sets based on the sequence of sticky ends. Multiple sticky end sequences are generated by virtue of offset cleavage using the recognition site added as part of the adaptor. Preferably this is accomplished by subjecting the nucleic acid sample to digestion by a restriction endonuclease that cleaves at a site different from the site of the recognition sequence. The fragments are indexed by adding an offset adaptor to newly generated ends. A different adaptor will be coupled to each different sticky end. The resulting fragments—which will have defined ends, are of equal lengths (in a preferred embodiment), and a central sequence derived from the source nucleic acid molecule—are binary sequence tags. The binary sequence tags can be used and further analyzed in numerous ways. For example, the binary sequence tags can be captured by hybridization and coupling, preferably by ligation, to a probe. The probe is preferably immobilized in an array or on sortable beads. The disclosed method differs from prior methods at least since the present method introduces an offset cleavage site into target nucleic fragment. This has the advantage that sets of sequence tags are generated that have defined lengths.

The method allows detection of the binary sequence tags where detection provides some sequence information for the tags including the sequence of the generated sticky end of each fragment, the recognition sequence of the nucleic acid cleaving reagent—preferably a restriction endonuclease—used to initially cleave nucleic acid molecules, and the central sequence of the tag. The set of binary sequence tags produced from a nucleic acid sample using particular nucleic acid cleaving reagents and adaptors will produce characteristic sets of binary sequence tags. The method allows a complex sample of nucleic acid to be cataloged quickly and easily in a reproducible and sequence-specific manner. The disclosed method also should produce two binary sequence tags for each cleavage site in the nucleic acid sample. This can allow comparisons and validation of a set of binary sequence tags.

One form of the BEST method, referred to as modification assisted analysis of binary sequence tags (MAABST), assesses modification of sequences in nucleic acid molecules by detecting differential cleavage based on the presence or absence of modification in the molecules. For example, a site that is methylated in a nucleic acid molecule will not be cut by a restriction enzyme that is sensitive to methylation at that site. A restriction enzyme that is insensitive to methylation will cleave at that site, thus producing a different pattern of binary sequence tags.

BRIEF DESCRIPTION OF THE DRAWINGS

FIGS. 1A, 1B, and 1C are a listing of examples of ligator-detectors (numbered sequences) designated for use with one of two example adaptor-indexers (FIG. 1A, top). The sticky end sequences (or their complements) are shown in bold.

DETAILED DESCRIPTION OF THE INVENTION

The disclosed method, referred to as Binary Encoded Sequence Tags (BEST), allows a complex sample of nucleic acid to be quickly and easily cataloged in a reproducible and sequence-specific manner. Such a catalog can be compared with other, similarly prepared catalogs of other nucleic acid samples to allow convenient detection of differences between the samples. The catalogs, which incorporate a significant amount of information about the nucleic acid samples, can serve as fingerprints of the nucleic acid samples which can be used both for detection of related nucleic acid samples and comparison of nucleic acid samples. For example, the presence or identity of specific organisms can be detected by producing a catalog of nucleic acid of the test organism and comparing the resulting catalog with reference catalogs prepared from known organisms. Changes and differences in gene expression patterns can also be detected by preparing catalogs of mRNA from different cell samples and comparing the catalogs. The catalog of sequences can also be used to produce a set of probes or primers that is specific for the source of a nucleic acid sample.

Comparison of nucleic acid catalogs produced with the disclosed method is facilitated by the ordered nature of the sequence information produced and cataloged in the method. Use of immobilization, sorting, and/or array detection in the method allows automation of the method, the cataloging of the information, and comparisons to other catalogs. The method can result in the equivalent of a large number of sequence-specific bins that can be filled, empty, or filled to different levels, with the pattern of filled and empty bins, and/or of the amount of signal in a bin, providing information about the nucleic acid sample that has been cataloged. There is no need to assemble overlapping sequence strings into larger sequences (although this can be done). Rather, the individual sequences detected are themselves data points in the catalog.

The BEST method involves the following basic steps. A nucleic acid sample is incubated with one or more nucleic acid cleaving reagents, preferably restriction endonucleases, that results in a set of DNA fragments cleaved at particular sites. The sample is then mixed with one or more offset adaptors, each of which has a recognition sequence for a nucleic acid cleaving reagent that cleaves at a site offset from the recognition sequence. The offset adaptors are then covalently coupled, preferably by ligation, onto the DNA fragments. The offset adapters should have ends compatible with the ends of the nucleic acid fragments. Coupling, both here and in other steps, can be accomplished using any suitable technique, including ligation and chemical reactions. Ligation is preferred. When coupling is by ligation, there should be a 5'-phosphate capable of participating in ligation on the appropriate strand.

The nucleic acid sample is incubated with one or more nucleic acid cleaving reagents, preferably restriction endonucleases, that cleave the nucleic acid fragments using the recognition sequence of the offset adaptors and that generate fragments having sticky ends with a variety of sequences. The fragments are preferably cleaved at the same distance from the recognition sequence. In one form of the method, the sample can be divided into aliquots (referred to as index samples); preferably as many aliquots as there are sticky end sequences. Where multiple restriction endonucleases are used, the nucleic acid sample is preferably divided into index samples before cleavage. Where a single restriction endonuclease is used, the nucleic acid sample is preferably divided into index samples following cleavage. The nucleic acid samples can also be divided into index samples following addition of the offset adaptor or adaptor-indexer. Index samples themselves can be further divided into secondary index samples.

Each sample (each index sample if the nucleic acid sample was divided) is then mixed with one or more adaptor-indexers, each of which has a sticky end compatible with one of the possible sticky ends on the DNA fragments in that index sample. It is preferred that a different adaptor-indexer be mixed with each index sample. The adaptor-indexers are then covalently coupled, preferably by ligation, onto compatible DNA fragments. The resulting nucleic acid fragments are binary sequence tags.

The binary sequence tags can be analyzed in a variety of ways. For example, the binary sequence tags can be amplified, detected, identified, sequenced, cataloged, or a combination. Preferably the binary sequence tags are detected, preferably by determining, directly or indirectly, the presence, amount, presence and amount, or absence of one or more binary sequence tags. Numerous techniques and methods are known for the analysis of nucleic acid fragments which are suitable for analysis of binary sequence tags.

A preferred form of binary sequence tag analysis is indexed probe hybridization. This can be accomplished by hybridizing the binary sequence tags in each sample (or index sample) to ligator-detectors. One end of each ligator-detector has sequence matching or complementary to all or part of one of the possible sticky end sequences generated by the second nucleic acid cleaving reagent. The ligator-detector can, and preferably does, have sequence matching or complementary to all or part of the sequence adjacent to the sticky end sequence in the fragment coupled to the adaptor-indexer. The ligator-detector used in each index sample preferably matches or is complementary to all or part of the sequence, including sticky end sequence, in the adaptor-indexer sequence used in that index sample. Each sample (or index sample) is reacted with and coupled, preferably by ligation, to one or more detector probes. Preferably, the set of detector probes used include every possible sequence of a given length (for example, every possible six base sequence). The ends of the probes and the ligator-detectors are coupled only if the probe hybridizes adjacent to the end of the ligator-adaptor. The probes are preferably immobilized oligonucleotides.

Each binary sequence tag processed through indexed probe hybridization will result in a signal based on coupling of the ligator-detector to a probe. A complex nucleic acid sample will produce a unique pattern of signals. It is this pattern that allows unique cataloging of nucleic acid samples and sensitive and powerful comparisons of the patterns of signals produced from different nucleic acid samples.

Coupling of ligator-detectors to probes can be detected directly or indirectly. For example, any of the probe, the ligator-detector, or the associated adaptor-indexer or offset adaptor can be detected. Association of a ligator-detector, adaptor-indexer, or offset adaptor with a given probe is indicative of coupling of the probe and ligator-detector. Detection of such associations can be facilitated through immobilization of the probes, detector-ligators, adaptor-indexers, or offset adaptors, and through the use of capture tags, sorting tags and detectable labels in association with the probes, detector-ligators, adaptor-indexers and/or offset adaptors. Any combination of immobilization and association with capture tags, sorting tags, and labels can be used. Preferably, the probes are immobilized in arrays and the ligator-detectors are associated with a detectable label. Thus, detection of a signal at a particular location in a particular array of immobilized probes can provide information about nucleic acid fragments indexed from the nucleic acid sample.

Where the probes are immobilized in arrays, the array, and location in the array, where a DNA fragment generates a signal identify the sequence of the sticky end of the DNA fragment and of the sequence adjacent to the sticky end. This is a ten base sequence when a four base sticky end and six base immobilized probes are used. The fixed relationship between the recognition sequence and the cleavage site of the Type IIS restriction enzyme (when used) and the identity of the recognition sequence, provide additional sequence information about the DNA fragment. The same effect can be accomplished by otherwise capturing, sorting, or detecting particular probes (via capture tags, sorting tags, and labels). That is, so long as the probe and the ligator-detector coupled to it can be identified, a pattern can be determined.

Binary sequence tags produced using the disclosed method generally occur in correlated pairs, except in a few cases where the initial cleavage site occurs near the terminus of a DNA substrate. Analysis of the tag catalogs using the disclosed method can reveal, within certain confidence limits, the identity of a subset of the correlated pairs. The identification of the subset of correlated pairs provides additional sequence information about the catalog of tags.

One form of the BEST method, referred to as modification assisted analysis of binary sequence tags (MAABST), assesse's modification of sequences in nucleic acid molecules by detecting differential cleavage based on the presence or absence of modification in the molecules. For example, a site that is methylated in a nucleic acid molecule will not be cut by a restriction enzyme that is sensitive to methylation at that site. A restriction enzyme that is insensitive to methylation will cleave at that site, thus producing a different pattern of sequence tags.

Materials

Nucleic Acid Samples

Any nucleic acid sample can be used with the disclosed method. Examples of suitable nucleic acid samples include genomic samples, mRNA samples, cDNA samples, nucleic acid libraries (including cDNA and genomic libraries), whole cell samples, environmental samples, culture samples, tissue samples, bodily fluids, and biopsy samples. Numerous other sources of nucleic acid samples are known or can be developed and any can be used with the disclosed method. Preferred nucleic acid samples for use with the disclosed method are nucleic acid samples of significant complexity such as genomic samples and mRNA samples.

Nucleic acid fragments are segments of larger nucleic acid molecules. Nucleic acid fragments, as used in the disclosed method, generally refer to nucleic acid molecules that have been cleaved. A nucleic acid sample that has been incubated with a nucleic acid cleaving reagent is referred to as a digested sample. A nucleic acid sample that has been digested using a restriction enzyme is referred to as a digested sample.

An index sample is a nucleic acid sample that has been divided into different aliquots for further processing. In the context of the disclosed method, index samples are preferably aliquots of a digested nucleic acid sample to which different adaptor-indexers are added for coupling, preferably by ligation, to nucleic acid fragments present in the digested sample. In the disclosed method, different nucleic acid fragments are processed in the different index samples based on the sticky end sequence of the fragments. Thus, it is preferred that digested nucleic acid samples be divided into as many index samples as the number of possible sticky end sequences generated by the nucleic acid cleaving reagent used to digest the sample. Where multiple different nucleic acid cleaving reagents are used to cleave a nucleic acid sample, it is preferred that the nucleic acid sample be divided into as many aliquots as nucleic acid cleaving reagents used and that the nucleic acid sample be divided prior to cleavage. Where multiple restriction endonucleases are used, the nucleic acid sample is preferably divided into index samples before cleavage. Where a single restriction endonuclease is used, the nucleic acid sample is preferably divided into index samples following cleavage. The nucleic acid samples can also be divided into index samples following addition of the offset adaptor or adaptor-indexer. Index samples themselves can be further divided into secondary index samples.

A control nucleic acid sample is a nucleic acid sample to which another nucleic acid sample (which can be referred to as a tester nucleic acid sample) is to be compared. A control index sample is an index sample to which another index sample (which can be referred to as a tester index sample) is to be compared.

Nucleic Acid Cleaving Reagents

The disclosed method makes use of nucleic acid cleaving reagents. Nucleic acid cleaving reagents are compounds, complexes, and enzymes that cause, mediate, or catalyze cleavage on nucleic acid molecules. Preferred nucleic acid cleaving reagents are those that cleave nucleic acid molecules in a sequence-specific manner. Restriction enzymes (also referred to as restriction endonucleases) are the preferred form of nucleic acid cleaving reagents. Other nucleic acid cleaving reagents include the universal restriction endonucleases of Szybalski (Szybalski, *Gene* 40(2–3):169–73 (1985); Podhajska and Szybalski, *Gene* 40(2–3):175–82 (1985)[published erratum appears in *Gene* 43(3):325 (1985)]), the advanced DNA cleavage systems developed by Breaker et al. (Carmi et al., *Proc Natl Acad Sci USA* 95(5):2233–2237 (1998)), and the use of zinc fingers to direct site recognition of restriction enzymes such as the hybrid restriction enzymes described by Kim et al., *Proc. Natl. Acad. Sci. USA* 93(3):1156–1160 (1996), and Smith et al., *Nucleic Acids Res.* 27(2):674–681 (1999).

Many nucleic acid cleaving reagents are known and can be used with the disclosed method. Relevant to the disclosed method, nucleic acid cleaving reagents generally have a recognition sequence and a cleavage site. Many nucleic acid cleaving reagents, especially restriction enzymes, also generate sticky ends at the cleavage site. A recognition sequence is the nucleotide sequence which, if present in a nucleic acid molecule, will direct cleavage of the nucleic acid molecule by a cognate nucleic acid cleaving reagent. The cleavage site of a nucleic acid cleaving reagent is the site, usually in relation to the recognition sequence, where the nucleic acid cleaving reagent cleaves a nucleic acid molecule. Sticky ends (also referred to as cohesive ends, protruding ends, and 5' or 3' overhangs) are single-stranded nucleic acid segments at the end of a double-stranded nucleic acid segment.

For specific embodiments of the method, the nucleic acid cleaving reagents used will have certain properties and/or certain relationships to other restriction enzymes used in the method. For example, in some preferred embodiments of the disclosed method, nucleic acid cleaving reagents that generate sticky ends having a plurality of different sequences are preferred, with nucleic acid cleaving reagents having a cleavage site offset from the recognition sequence being most preferred. Other embodiments of the disclosed method require the use of different nucleic acid cleaving reagents that have different recognition sequences and/or generate different sticky ends than other nucleic acid cleaving reagents used on the same index sample at other stages in the method. For example, where multiple digests (that is, cleavage reactions) are used in the method, it is preferred that the nucleic acid cleaving reagents used in each of the digests have a recognition sequence different from that of the nucleic acid cleaving reagents used in the other digests. In such cases, the known properties of nucleic acid cleaving reagents can be used to select or design appropriate nucleic acid cleaving reagents.

Where a nucleic acid cleaving reagent cleaves DNA at a site different or offset from the recognition sequence, a variety of sticky ends having different sequences can be generated. This is because recognition sequences in nucleic acids can occur next to any sequence and therefore the site of cleavage can have any sequence. For example, FokI cleaves 9 (upper strand) and 13 (lower strand) nucleotides downstream from the recognition site of GGATG. The four base sticky end will have whatever sequence happens to be 10 to 13 nucleotides away from the recognition site. Given enough cleavage sites, a total of 256 different sticky end sequences (that is every possible four base sequence) can result from a FokI digestion. As a result, restriction enzymes such as Type IIS restriction enzymes can be said to generate sticky ends having a plurality of different sequences.

As used herein, unless otherwise indicated, the terms digest, digestion, digested, and digesting refer generally to a cleavage reaction or the act of cleaving and is not intended to be limited to cleavage by a protein enzyme or by any particular mechanism. Similarly, the term restricted is intended to refer to any nucleic acid cleavage, not just cleavage by a restriction enzyme. In the context of nucleic acid cleaving reagents, sequence-specific requires only some sequence specificity, not absolute sequence specificity. That is, nucleic acid cleaving reagents having a completely or partially defined recognition sequence are preferred. Thus, nucleic acid cleaving reagents having some degeneracy in their recognition sequence are still considered sequence-specific.

A first nucleic acid cleaving reagent is a nucleic acid cleaving reagent used first to digest a nucleic acid sample. A second nucleic acid cleaving reagent is a nucleic acid cleaving reagent used to digest a fragment to which an offset adaptor has been coupled. First nucleic acid cleaving reagents are preferably Type II restriction endonucleases that cleave within the recognition sequence. Second nucleic acid cleaving reagents are preferably Type IIS restriction enzymes.

In addition to the use of restriction enzymes in a standard mode, the Type IIS enzymes can be used as universal restriction endonuclease as described by Szybalski (Szybalski, Gene 40(2–3):169–73 (1985); Podhajska and Szybalski, Gene 40(2–3):175–82 (1985)[published erratum appears in Gene 43(3):325 (1985)]). In the Szybalski technique single-stranded or double-stranded DNA can be cleaved at any arbitrary (but specific) site utilizing the structure described in combination with a Type IIS enzyme. More advanced DNA cleavage systems developed by Breaker et al. (Carmi et al., Proc Natl Acad Sci USA 95(5):2233–2237 (1998)). In these systems Breaker has shown that DNA recognize a particular sequence in a target DNA and can cleave the target DNA, single-stranded or double-stranded targets. With Breaker's system for evolution of DNA for a particular action, it is clear that given reasonable time and effort a suitable DNA for a recognition and particular cleavage result is practical.

Offset Adaptors

Offset adaptors are double-stranded nucleic acids that contain a recognition site for a nucleic acid cleaving reagent that cleaves at a site offset from the recognition site. Offset adaptors preferably contain a single-stranded portion and a double-stranded portion. The single-stranded portion is at one end of the offset adaptor and constitutes a sticky end. It is preferable that the protruding single strand (sticky end) have two, three, four, or five nucleotides. The double-stranded portion of offset adaptor may have any convenient sequence or length. In general, the sequence and length of the double-stranded portion is selected to be adapted to subsequent steps in the method. For example, sequences in the offset adaptor may be used for primer or probe hybridization. If the fragments in the samples to which adaptors have been ligated are to be amplified, the offset adaptors can provide sequence for primer hybridization. Thus, preferred sequence composition and length for the double-stranded portion of offset adaptors will generally be those that are useful for primer hybridization.

It is preferred that offset adaptors not have any sequences that are self-complementary. It is considered that this condition is met if there are no complementary regions greater than six nucleotides long without a mismatch or gap. A set of offset adaptors for use in the disclosed method can include different offset adaptors where the single-stranded portions each have a different nucleotide sequence compatible with a sticky end sequence generated by one of the first restriction enzymes. It is preferable that the members of a set of offset adaptors contain a double-stranded portion which is identical for each member of the set.

Offset adaptors can also contain or be associated with capture tags to facilitate immobilization or capture of fragments to which offset adaptors have been coupled. Offset adaptors can also contain or be associated with sorting tags to facilitate sorting or separation of fragments to which offset adaptors have been coupled. Offset adaptors can also contain or be associated with labels to facilitate detection of fragments to which offset adaptors have been coupled. Offset adaptors can also be immobilized on a substrate.

Offset adaptors can also include a protruding end at the end opposite the sticky end. Such an end can be used as, for example, a hybridization target for a label to be associated with the offset adaptor (and thus can be considered the detection portion of the offset adaptor). The two strands of an offset adaptor can be used separately in the disclosed method. For example, the two strands of the offset adaptor can be coupled to a nucleic acid fragment separately. Offset adaptors can also include one or more photocleavable nucleotides to facilitate release of adaptor-indexer sequences for detection. Photocleavable nucleotides and their use are described in WO 00/04036.

Offset adaptors need not be composed of naturally occurring nucleotides. Modified nucleotides, unnatural bases and nucleotide and oligonucleotide analogs can be used. All that is required is that the offset adaptor have the general structure described herein and be capable of the interactions and reactions required in the disclosed method.

Adaptor-Indexers

Adaptor-indexers are double-stranded nucleic acids containing a single-stranded portion and a double-stranded portion. The single-stranded portion is at one end of the adaptor-indexer and constitutes a sticky end. The sticky end is referred to as the sticky end portion of the adaptor-indexer. It is preferable that the protruding single strand (sticky end) have two, three, four, or five nucleotides. The double-stranded portion of adaptor-indexers may have any convenient sequence or length. In general, the sequence and length of the double-stranded portion is selected to be adapted to subsequent steps in the method. For example, sequences in the adaptor-indexer may be used for primer or probe hybridization. A preferred purpose of adaptor-indexers is to provide sequence for hybridization by a ligator-detector. If the fragments in the samples to which adaptors have been coupled are to be amplified, the adaptor-indexers can also provide sequence for primer hybridization (which can overlap or be contiguous with sequence for ligator-detector hybridization). Thus, preferred sequence composition and length for the double-stranded portion of adaptor-indexers will generally be those that are useful for probe and primer hybridization. Adaptor-indexers can also include a detector portion which is designed to facilitate detection of the adaptor-indexer. The detection portion can be, for example, a sequence that is a hybridization target or it can be a label or tag.

Generally, the sequence of the double-stranded portion of an adaptor-indexer should not include the recognition sequence of any restriction enzyme to be used in a subsequent step in the method. It is preferred that adaptor-indexers not have any sequences that are self-complementary. It is considered that this condition is met if there are no complementary regions greater than six nucleotides long without a mismatch or gap.

A set of adaptor-indexers for use in the disclosed method should include different adaptor-indexers where the single-stranded portion each have a different nucleotide sequence selected from combinations and permutations of the nucleotides A, C, G, and T. Where multiple nucleic acid cleaving reagents are used in the first digest, the single-stranded portion of each adaptor-indexer can have a different nucleotide sequence compatible with a sticky end sequence generated by one of the nucleic acid cleaving reagents. While the sticky ends of adaptor-indexers in one set have different sequences, it is preferred that they be of the same length to facilitate use of the set to index fragments produced by cleavage by one nucleic acid cleaving reagent. It is preferable that the members of a set of adaptor-indexers contain a double-stranded portion which is identical for each member of the set. However, members of a set of adaptor-indexers can also have double-stranded portions that differ in some way. Similarly, some of the adaptor-indexers in a set can have identical double-stranded portions while others in the same set have different double-stranded portions. Different configurations of the set can be used to produce different types of data or probe particular relationships between tags in the disclosed method.

A preferred set of indexing linker strands comprising: (a) at least two single-stranded first oligonucleotides each having a common identical sequence, and a unique sequence of a length selected from 2, 3, 4 and 5 nucleotides selected from permutations and combinations of A, G, C and T nucleotides, at one end selected from a 3' end and a 5' end; and (b) a single-stranded second oligonucleotide whose sequence is complementary to the common sequence of the first oligonucleotides such that, when hybridized with any one of the first oligonucleotides, a double-stranded adaptor-indexer would result which includes an end having a sticky end with a unique sequence.

Adaptor-indexers can also contain or be associated with capture tags to facilitate immobilization or capture of fragments to which adaptor-indexers have been coupled. In general, the capture tag can be one member of a binding pair such as biotin and streptavidin. Capture tags are discussed more fully elsewhere herein. Adaptor-indexers can also contain or be associated with sorting tags to facilitate sorting or separation of fragments to which adaptor-indexers have been coupled. In general, the sorting tag can be a detectable label such as a fluorescent moiety or a manipulatable moiety such as a magnetic bead. Sorting tags are discussed more fully elsewhere herein. Adaptor-indexers can also contain or be associated with labels to facilitate detection of fragments to which adaptor-indexers have been coupled. Adaptor-indexers can also be immobilized on a substrate.

Adaptor-indexers can also include a protruding end at the end opposite the sticky end. Such an end can be used as, for example, a hybridization target for a label to be associated with the adaptor-indexer (and thus can be considered the detection portion of the adaptor-indexer). The two strands of an adaptor-indexer can be used separately in the disclosed method. For example, the two strands of the adaptor-indexer can be coupled to a nucleic acid fragment separately. Adaptor-indexers can also include one or more photocleavable nucleotides to facilitate release of adaptor-indexer sequences for detection. Photocleavable nucleotides and their use are described in WO 00/04036.

Adaptor-indexers need not be composed of naturally occurring nucleotides. Modified nucleotides, unnatural bases and nucleotide and oligonucleotide analogs can be used. All that is required is that the adaptor-indexer have the general structure described herein and be capable of the interactions and reactions required in the disclosed method.

Ligator-Detectors

A ligator-detector is a nucleic acid molecule containing a single-stranded region that is complementary to a portion of a binary sequence tag generated in the disclosed method from a nucleic acid sample. The ligator-detectors generally have a specific sequence relationship to adaptor-indexers or offset adaptors. Ligator-detectors preferably include sequence-referred to as the detector portion of the ligator-detector—matching or complementary to all or part of sequence including, and adjacent to, the sticky end of at least one of the adaptor-indexers. Thus, the ligator-detector can have sequence matching or complementary to sequence in the nucleic acid fragment adjacent to the sticky end sequence (on either or both sides), matching or complementary to the sticky end, or sequence matching or complementary to both sequence in the nucleic acid fragment adjacent to the sticky end sequence and the sticky end.

Preferably, the sequence of a ligator-detector matches or is complementary to all or part of a sticky end sequence and all or part of the adjacent sequence of the adaptor-indexer designed for use with that sticky end sequence. In this form, the sequence of a ligator-detector matches or is complementary to all or part of the recognition sequence of the first restriction enzyme(s) when cleavage is not offset from the recognition sequence. Alternatively, the ligator-detector can include sequence matching or complementary to sequence in the nucleic acid fragment adjacent to the sticky end sequence on the offset adaptor side. Whether the sequence in the ligator-detector is matching or complementary determines which strand of the adaptor-indexer and/or fragment will hybridize to the detector-ligator. It is preferred that only one type of ligator-detector—matching or complementary— is used in a given reaction of the disclosed method.

Some examples of sequence relationships between adaptor-indexers and ligator detectors are illustrated in FIG. 1. Ligator-detectors 1–12 in FIG. 1 are designed to match all or part of the sticky end sequence of adaptor-indexer I and all or part of the adjacent sequence of adaptor-indexer I. Ligator-detectors 13–19 are designed to be complementary to all or part of the sticky end sequence of adaptor-indexer I and all or part of the adjacent sequence of adaptor-indexer I. Ligator-detectors 21–32 are designed to match all or part of the sticky end sequence of adaptor-indexer II and all or part of the adjacent sequence of adaptor-indexer II. Ligator-detectors 33–40 are designed to be complementary to all or part of the sticky end sequence of adaptor-indexer II and all or part of the adjacent sequence of adaptor-indexer II. Note that the part of the adjacent sequence of the adaptor-indexer embodied in the ligator-detector is contiguous with the part of the sticky end sequence embodied in the ligator-detector. This is what is meant by adjacent.

Ligator-detectors 1–4 in FIG. 1 are designed to match all of the sticky end sequence of adaptor-indexer I and all or part of the adjacent sequence of adaptor-indexer I. Ligator-detectors 5–12 are designed to match part of the sticky end sequence of adaptor-indexer I and all or part of the adjacent sequence of adaptor-indexer I. Ligator-detectors 2–4 and 8–12 are designed to match all or part of the sticky end sequence of adaptor-indexer I and part of the adjacent sequence of adaptor-indexer I. Ligator-detectors 13–16 are designed to be complementary to all of the sticky end sequence of adaptor-indexer I and all or part of the adjacent sequence of adaptor-indexer I. Ligator-detectors 17–19 are designed to be complementary to part of the sticky end sequence of adaptor-indexer I and all or part of the adjacent sequence of adaptor-indexer I. Ligator-detectors 14–16 are designed to be complementary to all or part of the sticky end sequence of adaptor-indexer I and part of the adjacent sequence of adaptor-indexer I. Ligator-detector 20 is designed to match all of the recognition sequence of the restriction enzyme (which generates a sticky end compatible with the sticky end of adaptor-indexer I), and all of the adjacent sequence of adaptor-indexer I. Note the extra nucleotide extending beyond the adaptor-indexer sticky end sequence. This is a flanking nucleotide in the recognition sequence.

Ligator-detectors 21–24 are designed to match all of the sticky end sequence of adaptor-indexer II and all or part of the adjacent sequence of adaptor-indexer II. Ligator-detectors 25–32 are designed to match part of the sticky end sequence of adaptor-indexer II and all or part of the adjacent sequence of adaptor-indexer II. Ligator-detectors 22–24 and 28–31 are designed to match all or part of the sticky end sequence of adaptor-indexer II and part of the adjacent sequence of adaptor-indexer II. Ligator-detectors 33–36 are designed to be complementary to all of the sticky end sequence of adaptor-indexer II and all or part of the adjacent sequence of adaptor-indexer II. Ligator-detectors 37–40 are designed to be complementary to part of the sticky end sequence of adaptor-indexer II and all or part of the adjacent sequence of adaptor-indexer II. Ligator-detectors 34–36 and 40 are designed to be complementary to all or part of the sticky end sequence of adaptor-indexer II and part of the adjacent sequence of adaptor-indexer II.

Where the nucleic acid cleaving reagents used in the first digest cleave within the recognition sequence for the nucleic acid cleaving reagent such that the recognition sequence extends beyond the sticky end sequence, the ligator-detector can also match or be complementary to all or part of the recognition sequence. Where the recognition sequence extends beyond the sticky end sequence (for example, six-base recognition sequence and four-base sticky end), the ligator-detector sequence can extend beyond the sticky end sequence of its cognate adaptor-indexer. An example of such a ligator-detector is illustrated in FIG. 1 (ligator-detector number 20).

While the ligator-detector can be detected using sequence-based detection systems, the ligator-detectors can also contain a label to facilitate detection of the ligator-detector. Numerous labels are known and can be used for this purpose. Ligator-detectors can also contain or be associated with capture tags to facilitate immobilization or capture of the ligator-detectors. Ligator-detectors can also contain or be associated with sorting tags to facilitate sorting or separation of the ligator-detectors. Ligator-detectors can also be immobilized on a substrate.

Ligator-detectors can also include one or more photo-cleavable nucleotides to facilitate release of ligator-detector sequences for detection. Photocleavable nucleotides and their use are described in WO 00/04036.

Ligator-detectors need not be composed of naturally occurring nucleotides. Modified nucleotides, unnatural based and nucleotide and oligonucleotide analogs can be used. All that is required is that the ligator-detector have the general structure described herein and be capable of the interactions and reactions required in the disclosed method.

Adaptor-indexer I in FIG. 1 is composed of nucleotides 2–25 of SEQ ID NO:1 (top strand) and nucleotides 1–20 of SEQ ID NO:2 (bottom strand). Adaptor-indexer II is composed of nucleotides 5–24 of SEQ ID NO:3 (top strand) and SEQ ID NO:4 (bottom strand). Ligator-detector I is nucleotides 2–25 of SEQ ID NO:1. Ligator-detector 2 is nucleotides 2–24 of SEQ ID NO:1. Ligator-detector 3 is nucleotides 2–21 of SEQ ID NO:1. Ligator-detector 4 is nucleotides 2–18 of SEQ ID NO:1. Ligator-detector 5 is nucleotides 3–25 of SEQ ID NO:1. Ligator-detector 6 is nucleotides 4–25 of SEQ ID NO:1. Ligator-detector 7 is nucleotides 5–25 of SEQ ID NO:1. Ligator-detector 8 is nucleotides 3–24 of SEQ ID NO:1. Ligator-detector 9 is nucleotides 3–23 of SEQ ID NO:1. Ligator-detector 10 is nucleotides 3–20 of SEQ ID NO:1. Ligator-detector 11 is nucleotides 3–18 of SEQ ID NO:1. Ligator-detector 12 is nucleotides 4–22 of SEQ ID NO:1. Ligator-detector 13 is SEQ ID NO:2. Ligator-detector 14 is nucleotides 2–24 of SEQ ID NO:2. Ligator-detector 15 is nucleotides 4–24 of SEQ ID NO:2. Ligator-detector 16 is nucleotides 9–24 of SEQ ID NO:2. Ligator-detector 17 is nucleotides 1–23 of SEQ ID NO:2. Ligator-detector 18 is nucleotides 1–22 of SEQ ID NO:2. Ligator-detector 19 is nucleotides 1–21 of SEQ ID NO:2. Ligator-detector 20 is SEQ ID NO:1. Ligator-detector 21 is SEQ ID NO:3. Ligator-detector 22 is nucleotides 1–23 of SEQ ID NO:3. Ligator-detector 23 is nucleotides 1–21 of SEQ ID NO:3. Ligator-detector 24 is nucleotides 1–15 of SEQ ID NO:3. Ligator-detector 25 is nucleotides 2–24 of SEQ ID NO:3. Ligator-detector 26 is nucleotides 3–24 of SEQ ID NO:3. Ligator-detector 27 is nucleotides 4–24 of SEQ ID NO:3. Ligator-detector 28 is
nucleotides 2–23 of SEQ ID NO:3. Ligator-detector 29 is
nucleotides 2–21 of SEQ ID NO:3. Ligator-detector 30 is
nucleotides 2–19 of SEQ ID NO:3. Ligator-detector 31 is
nucleotides 2–16 of SEQ ID NO:3. Ligator-detector 32 is
nucleotides 3–24 of SEQ ID NO:3. Ligator-detector 33 is
SEQ ID NO:4. Ligator-detector 34 is nucleotides 2–24 of
SEQ ID NO:4. Ligator-detector 35 is nucleotides 4–24 of
SEQ ID NO:4. Ligator-detector 36 is nucleotides 9–24 of
SEQ ID NO:4. Ligator-detector 37 is nucleotides 1–23 of
SEQ ID NO:4. Ligator-detector 38 is nucleotides 1–22 of
SEQ ID NO:4. Ligator-detector 39 is nucleotides 1–21 of
SEQ ID NO:4. Ligator-detector 40 is nucleotides 5–23 of
SEQ ID NO:4.

Detector Probes

Detector probes are molecules, preferably oligonucleotides, that can hybridize to nucleic acids in a sequence-specific manner. In the disclosed method, detector probes are used to capture ligator-detectors based on complementary sequences present in sample nucleic acid fragments to which the ligator-detectors are hybridized. Detector probes are preferably used in sets having a variety of probe sequences, preferably a set of probes having every possible combination (or hybridizable to every combination) of nucleotide sequence the length of the probe. Detector probes are preferably used in sets where each probe has the same length. Preferred lengths for the probe portion of detector probes are five, six, seven, and eight nucleotides. Detector probes preferably include a probe portion (for hybridization to sample fragments) and linker portions through which the probe portion is coupled to a substrate, capture tag, sorting, tag, or label. These linker portions can have any suitable structure and will generally be chosen based on the method of immobilization or synthesis of the detector probes. The linker portion can be made up of or include nucleotides. The linker portions can have any suitable length and preferably are of sufficient length to allow the probe portion to hybridize effectively. For convenience and unless otherwise indicated, reference to the length of detector probes refers to the length of the probe portion of the probes. Immobilized detector probes are detector probes immobilized on a support.

Detector probes can be, and preferably are, immobilized on a substrate. Detector probes can also contain or be associated with capture tags to facilitate immobilization or capture of the probes and ligator-detectors to which they have been coupled. Detector probes can also contain or be associated with sorting tags to facilitate sorting or separation of the probes and ligator-detectors to which they have been coupled. Detector probes can also contain or be associated with labels to facilitate detection of the probes and ligator-detectors to which they have been coupled.

Detector probes can also include one or more photocleavable nucleotides to facilitate release of probe sequences and ligator-detectors coupled to the probe. Photocleavable nucleotides and their use are described in WO 00/04036.

Detector probes need not be composed of naturally occurring nucleotides. Modified nucleotides, unnatural based and nucleotide and oligonucleotide analogs can be used. All that is required is that the probe have the general structure described herein and be capable of the interactions and reactions required in the disclosed method.

Probe Arrays

Different detector probes can be used together as a set. The set can be used as a mixture of all or subsets of the probes, probes used separately in separate reactions, or immobilized in an array. Probes used separately or as mixtures can be physically separable through, for example, the use of capture tags, sorting tags, or immobilization on beads. A probe array (also referred to herein as an array) includes one or more probes or a plurality of probes immobilized at identified or predetermined locations on the array. In this context, plurality of probes refers to multiple probes each having a different sequence. Each predetermined location on the array has one type of probe (that is, all the probes at that location have the same sequence). Each location preferably will have multiple copies of the probe. The spatial separation of probes of different sequence in the array allows separate detection and identification of ligator-detectors that become coupled to the probes via hybridization of the probes to nucleic acid fragments in a nucleic acid sample. If a ligator-detector is detected at a given location in a probe array, it indicates that the sequence adjacent to the site in the nucleic acid fragment where the ligator-detector hybridized is complementary to the probe immobilized at that location in the array.

Adaptor-indexers, ligator-detectors, and offset adaptors can also be immobilized in arrays. Different modes of the disclosed method can be performed with different components immobilized, labeled, or tagged. Arrays of adaptor-indexers, ligator-detectors, and offset adaptors can be made and used as described below and elsewhere herein for the detector probes.

Solid-state substrates for use in probe arrays can include any solid material to which oligonucleotides can be coupled, directly or indirectly. This includes materials such as acrylamide, cellulose, nitrocellulose, glass, silicon, polystyrene, polyethylene vinyl acetate, polypropylene, polymethacrylate, polyethylene, polyethylene oxide, glass, polysilicates, polycarbonates, teflon, fluorocarbons, nylon, silicon rubber, polyanhydrides, polyglycolic acid, polylactic acid, polyorthoesters, polypropylfumerate, collagen, glycosaminoglycans, and polyamino acids. Solid-state substrates can have any useful form including thin films or membranes, beads, bottles, dishes, fibers, woven fibers, shaped polymers, particles and microparticles. A preferred form for a solid-state substrate is a microtiter dish. The most preferred form of microtiter dish is the standard 96-well type.

Methods for immobilization of oligonucleotides to solid-state substrates are well established. Detector probes can be coupled to substrates using established coupling methods. For example, suitable attachment methods are described by Pease et al., *Proc Natl. Acad. Sci. USA* 91(11):5022–5026 (1994), and Khrapko et al., *Mol Biol* (*Mosk*) (*USSR*) 25:718–730 (1991). A method for immobilization of 3'-amine oligonucleotides on casein-coated slides is described by Stimpson et al., *Proc. Natl. Acad. Sci. USA* 92:6379–6383 (1995). A preferred method of attaching oligonucleotides to solid-state substrates is described by Guo et al., *Nucleic Acids Res.* 22:5456–5465 (1994).

Methods for producing arrays of oligonucleotides on solid-state substrates are also known. Examples of such techniques are described in U.S. Pat. No. 5,871,928 to Fodor et al., U.S. Pat. No. 5,654,413 to Brenner, U.S. Pat. No. 5,429,807, and U.S. Pat. No. 5,599,695 to Pease et al.

Although preferred, it is not required that a given probe array be a single unit or structure. The set of probes may be distributed over any number of solid supports. For example, at one extreme, each probe may be immobilized in a separate reaction tube or container.

The probes in arrays can also be designed to have similar hybrid stability. This would make hybridization of fragments to detector probes more efficient and reduce the incidence of mismatch hybridization. The hybrid stability of probes can be calculated using known formulas and principles of thermodynamics (see, for example. Santa Lucia et al., *Biochemistry* 35:3555–3562 (1996); Freier et al., *Proc. Natl. Acad. Sci. USA* 83:9373–9377 (1986); Breslauer et al., *Proc Natl. Acad. Sci. USA* 83:3746–3750 (1986)). The hybrid stability of the probes can be made more similar (a process that can be referred to as smoothing the hybrid stabilities) by, for example, chemically modifying the probes (Nguyen et al., *Nucleic Acids Res.* 25(15):3059–3065 (1997); Hohsisel, *Nucleic Acids Res.* 24(3):430–432 (1996)). Hybrid stability can also be smoothed by carrying out the hybridization under specialized conditions (Nguyen et al., *Nucleic Acids Res.* 27(6):1492–1498 (1999); Wood et al., *Proc. Natl. Acad. Sci. USA* 82(6):1585–1588 (1985)).

Another means of smoothing hybrid stability of the probes is to vary the length of the probes. This would allow adjustment of the hybrid stability of each probe so that all of the probes had similar hybrid stabilities (to the extent possible). Since the addition or deletion of a single nucleotide from a probe will change the hybrid stability of the probe by a fixed increment, it is understood that the hybrid stabilities of the probes in a probe array will not be equal. For this reason, similarity of hybrid stability as used herein refers to any increase in the similarity of the hybrid stabilities of the probes (or, put another way, any reduction in the differences in hybrid stabilities of the probes). This is useful since any such increased similarity in hybrid stability can improve the efficiency and fidelity of hybridization and ligation of the detector probes.

The efficiency of hybridization and ligation of detector probes to sample fragments can also be improved by grouping detector probes of similar hybrid stability in sections or segments of a probe array that can be subjected to different hybridization conditions. In this way, the hybridization conditions can be optimized for particular classes of probes.

Amplification Primers

Amplification primers are oligolnucleotides used to amplify binary sequence tags. Amplification primers include sequence complementary to one of the strands of a binary sequence tag. This sequence is referred to as the complementary portion of the amplification primer. Preferably, the complementary portion of an amplification primer is complementary to all or a part of one of the strands of an adaptor-indexer, all or a part of one of the strands of an offset adaptor, all or a part of the double-stranded portion of an adaptor-indexer, or all or a part of the double-stranded portion of an offset adaptor. The complementary portion of an amplification primer can be any length that supports specific and stable hybridization between the primer and the primer complement portion. Generally this is 10 to 35 nucleotides long, but is preferably 16 to 20 nucleotides long.

It is preferred that amplification primers also contain additional sequence at the 5' end of the primer that is not complementary to any part of the binary sequence tag. This sequence is referred to as the non-complementary portion of the amplification primer. The non-complementary portion of an amplification primer may be any length, but is generally 1 to 100 nucleotides long. Amplifications primers need not be entirely single-stranded, but can contain a hairpin region formed between the 5' terminus and an internal sequence in the primer. Such amplifications primers are referred to herein as hairpin primers.

The amplification primer may also include modified nucleotides to make it resistant to exonuclease digestion or for other purposes. For example, the primer can have three or four phosphorothioate linkages between nucleotides at the 5' end of the primer. Amplification primers may contain deoxy-uridine residues that can be subsequently cleaved by an endonuclease. Amplification primers can also include one or more photocleavable nucleotides, to facilitate release of labels or mass tags in subsequent detection steps. Photocleavable nucleotides are described in WO 00/04036.

Amplification primers can also contain or be associated with capture tags to facilitate immobilization or capture of amplified sequence tags. In general, the capture tag can be one member of a binding pair such as biotin and streptavidin. Capture tags are discussed more fully elsewhere herein. Amplification primers can also contain or be associated with sorting tags to facilitate sorting or separation of amplified sequence tags. In general, the sorting tag can be a detectable label such as a fluorescent moiety or a manipulatable moiety such as a magnetic bead. Sorting tags are discussed more fully elsewhere herein. Amplification primers can also contain or be associated with labels to facilitate detection of amplified sequence tags. Amplification primers can also be immobilized on a substrate.

Amplification primers need not be composed of naturally occurring nucleotides. Modified nucleotides, unnatural based and nucleotide and oligonucleotide analogs can be used. All that is required is that the amplification primer have the general structure described herein and be capable of the interactions and reactions required in the disclosed method.

Anchored Primers

Anchored primers are oligonucleotides including an oligo dT portion and an anchor portion. The oligo dT portion is a string of dT residues at the 5' end of the primer. The anchor portion is one or more nucleotides at the 3' end of the primer that are not all dT. Anchored primers are useful for cDNA synthesis. Some forms of anchored primers are described by Liang et al., *Nucleic Acids Res,* 21(14): 3269–75 (1993), and Liang and Pardee, *Science* 257:967–971 (1992). A preferred form of anchored primer comprises 16 dT residues and 2 residues at the 3'-end other than TN. Examples of anchored primers are the sequences TTTTTTTTTTTTTTTTGC (SEQ ID NO:5), TTTTTTTTTTTTTTTTGT (SEQ ID NO:6), and TTTTTTTTTTTTTTTTCA (SEQ ID NO:7). There are 12 different primers of this type, each distinguished by the nucleotide sequence of the 3' terminal dinucleotide. Anchored primers are useful for generating a cDNA preparations of lower complexity. This is accomplished by performing reverse transcription in the presence of one anchored primer or in the presence of a set of anchored primers collectively having only a subset of the sequences possible. For example, six different cDNA preparations of reduced complexity may be generated by using six distinct sets of anchored primers, each set comprising only two of all the possible anchored primers ending in a unique non-TN dinucleotide as described above.

Labels

To aid in detection and quantitation of ligator-detectors coupled to detector probes, labels can be incorporated into, coupled to, or associated with, ligator-detectors, offset adaptors, detector probes, and/or adaptor-indexers. It is preferred that the ligator-detector be labeled. A label is any molecule that can be associated with ligator-detectors, directly or indirectly, and which results in a measurable, detectable signal, either directly or indirectly. A label is associated with a component when it is coupled or bound, either covalently or non-covalently, to the component. A label is coupled to a component when it is covalently coupled to the component. Many suitable labels for incorporation into, coupling to, or association with nucleic acid are known. Examples of labels suitable for use in the disclosed method are radioactive isotopes, fluorescent molecules, phosphorescent molecules, bioluminescent molecules, enzymes, antibodies, and ligands.

Examples of suitable fluorescent labels include fluorescein (FITC), 5,6-carboxymethyl fluorescein, Texas red, nitrobenz-2-oxa-1,3-diazol-4-yl (NBD), coumarin, dansyl chloride, rhodamine, 4'-6-diamidino-2-phenylinodole (DAPI), and the cyanine dyes Cy3, Cy3.5, Cy5, Cy5.5 and Cy7. Preferred fluorescent labels are fluorescein (5-carboxyfluorescein-N-hydroxysuccinimide ester) and rhodamine (5,6-tetramethyl rhodamine). Preferred fluorescent labels for simultaneous detection are FITC and the cyanine dyes Cy3, Cy3.5, Cy5, Cy5.5 and Cy7. The absorption and emission maxima, respectively, for these fluors are: FITC (490 nm; 520 nm), Cy3 (554 nm; 568 nm), Cy3.5 (581 nm; 588 nm), Cy5 (652 nm: 672 nm), Cy5.5 (682 nm; 703 nm) and Cy7 (755 nm; 778 nm), thus allowing their simultaneous detection. The fluorescent labels can be obtained from a variety of commercial sources, including Molecular Probes, Eugene, Oreg. and Research Organics, Cleveland, Ohio.

Labeled nucleotides are the preferred form of label since they can be directly incorporated into ligator-detectors during synthesis. Examples of labels that can be incorporated into DNA or RNA include nucleotide analogs such as BrdUrd (Hoy and Schimke, *Mutation Research* 290:217–230 (1993)), BrUTP (Wansick et al., *J. Cell Biology* 122:283–293 (1993)) and nucleotides modified with biotin (Langer et al., *Proc. Natl. Acad. Sci. USA* 78:6633 (1981)) or with suitable haptens such as digoxygenin (Kerkhof, *Anal. Biochem.* 205:359–364 (1992)). Suitable fluorescence-labeled nucleotides are Fluorescein-isothiocyanate-dUTP, Cyanine-3-dUTP and Cyanine-5-dUTP (Yu et al., *Nucleic Acids Res.*, 22:3226–3232 (1994)). A preferred nucleotide analog detection label for DNA is BrdUrd (BUDR triphosphate, Sigma), and a preferred nucleotide analog detection label for RNA is Biotin-16-uridine-5'-triphosphate (Biotin-16-dUTP, Boehringher Mannheim). Fluorescein, Cy3, and Cy5 can be linked to dUTP for direct labeling. Cy3.5 and Cy7 are available as avidin or anti-digoxygenin conjugates for secondary detection of biotin- or digoxygenin-labeled probes.

Labels that are incorporated into nucleic acid, such as biotin, can be subsequently detected using sensitive methods well-known in the art. For example, biotin can be detected using streptavidin-alkaline phosphatase conjugate (Tropix, Inc.), which is bound to the biotin and subsequently detected by chemiluminescence of suitable substrates (for example, chemiluminescent substrate CSPD: disodium, 3-(4-methoxyspiro-[1,2,-dioxetane-3-2'-(5'-chloro)tricyclo [3.3.1.1$^{3.7}$]decane]-4-yl)phenyl phosphate; Tropix, Inc.).

Other labels include molecular or metal barcodes, mass labels, and labels detectable by nuclear magnetic resonance, electron paramagnetic resonance, surface enhanced raman scattering, surface plasmon resonance, fluorescence, phosphorescence, chemiluminescence, resonance raman, microwave, or a combination. Mass labels are compounds or moieties that have, or which give the labeled component, a distinctive mass signature in mass spectroscopy. Mass labels are useful when mass spectroscopy is used for detection. Preferred mass labels are peptide nucleic acids and carbohydrates. Combinations of labels can also be useful. For example, color-encoded microbeads having, for example. 256 unique combinations of labels, are useful for distinguishing numerous components. For example, 256 different ligator-detectors can be uniquely labeled and detected allowing multiplexing and automation of the disclosed method.

Useful labels are described in de Haas et al., "Platinum porphyrins as phosphorescent label for time-resolved microscopy," *J. Histochem. Cytochem.* 45(9):1279–92 (1997); Karger and Gesteland, "Digital chemiluminescence imaging of DNA sequencing blots using a charge-coupled device camera," *Nucleic Acids Res.* 20(24):6657–65 (1992); Keyes et al., "Overall and internal dynamics of DNA as monitored by five-atom-tethered spin labels," *Biophys. J* 72(1):282–90 (1997); Kirschstein et al., "Detection of the DeltaF508 mutation in the CFTR gene by means of time-resolved fluorescence methods," *Bioelectrochem. Bioenerg.* 48(2):415–21 (1999); Kricka, "Selected strategies for improving sensitivity and reliability of immunoassays," *Clin. Chem.* 40(3):347–57 (1994); Kricka, "Chemiluminescent and bioluminescent techniques," *Clin. Chem.* 37(9): 1472–81 (1991); Kumke et al., "Temperature and quenching studies of fluorescence polarization detection of DNA hybridization," *Anal. Chem.* 69(3):500–6 (1997); McCreery, "Digoxigenin labeling," *Mol. Biotechnol.* 7(2):121–4 (1997); Mansfield et al., "Nucleic acid detection using non-radioactive labeling methods," *Mol. Cell Probes* 9(3): 145–56 (1995); Nurmi et al., "A new label technology for the detection of specific polymerase chain reaction products in a closed tube," *Nucleic Acids Res.* 28(8):28 (2000); Oetting et al. "Multiplexed short tandem repeat polymorphisms of the Weber 8A set of markers using tailed primers and infrared fluorescence detection," *Electrophoresis* 19(18) :3079–83(1998); Roda et al., "Chemiluminescent imaging of enzyme-labeled probes using an optical microscope-videocamera luminograph," *Anal. Biochem.* 257(1):53–62 (1998); Siddiqi et al., "Evaluation of electrochemiluminescence- and bioluminescence-based assays for quantitating specific DNA," *J. Clin. Lab. Anal.* 10(6):423–31 (1996); Stevenson et al., "Synchronous luminescence: a new detection technique for multiple fluorescent probes used for DNA sequencing," *Biotechniques* 16(6): 1104–11 (1994); Vo-Dinhl et al. "Surface-enhanced Raman gene probes," *Anal. Chem.* 66(20):3379–83 (1994); Volkers et al., "Microwave label detection technique for DNA in situ hybridization," *Eur. J Morphol.* 29(1):59–62 (1991).

Metal barcodes, a form of molecular barcode, are 30–300 nm diameter by 400–4000 nm multilayer multi metal rods. These rods are constructed by electrodeposition into an alumina mold, then the alumina is removed leaving these small multilayer objects behind. The system can have up to 12 zones encoded, in up to 7 different metals, where the metals have different reflectivity and thus appear lighter or darker in an optical microscope depending on the metal; this leads to practically unlimited identification codes. The metal bars can be coated with glass or other material, and probes attached to the glass using methods commonly known in the art; assay readout is by fluorescence from the target, and the identity of the probe is from the light dark pattern of the barcode.

Methods for detecting and measuring signals generated by labels are known. For example, radioactive isotopes can be detected by scintillation counting or direct visualization; fluorescent molecules can be detected with fluorescent spectrophotometers; phosphorescent molecules can be detected with a spectrophotometer or directly visualized with a camera; enzymes can be detected by measurement or visualization of the product of a reaction catalyzed by the enzyme; antibodies can be detected by detecting a secondary detection label coupled to the antibody. Such methods can be used directly in the disclosed method of amplification and detection. As used herein, detection molecules are molecules which interact with amplified nucleic acid and to which one or more detection labels are coupled. In another form of detection, labels can be distinguished temporally via different fluorescent, phosphorescent, or chemiluminescent emission lifetimes. Multiplexed time-dependent detection is described in Squire et al., J. Microscopy 197(2):136–149 (2000), and WO 00/08443.

Quantitative measurement of the amount or intensity of a label can be used. For example, quantitation can be used to determine if a given label, and thus the labeled component, is present at a threshold level or amount. A threshold level or amount is any desired level or amount of signal and can be chosen to suit the needs of the particular form of the method being performed.

Capture Tags

A capture tag is any compound that can be used to separate compounds or complexes having the capture tag from those that do not. Preferably, a capture tag is a compound, such as a ligand or hapten, that binds to or interacts with another compounds such as ligand-binding molecule or an antibody. It is also preferred that such interaction between the capture tag and the capturing component be a specific interaction, such as between a hapten and an antibody or a ligand and a ligand-binding molecule. Capture tags preferably are antibodies, ligands, binding proteins, receptor proteins, haptens, aptamers, carbohydrates, synthetic polyamides, or oligonucleotides. Preferred binding proteins are DNA binding proteins. Preferred binding proteins are DNA binding proteins. Preferred DNA binding proteins are zinc finger motifs, leucine zipper motifs, helix-turn-helix motifs. These motifs can be combined in the same specific binding molecule.

Preferred capture tags, described in the context of nucleic acid probes, are described by Syvnen et al., *Nucleic Acids Res.*, 14:5037 (1986). Preferred capture tags include biotin, which can be incorporated into nucleic acids. In the disclosed method, capture tags incorporated into adaptor-indexers or offset adaptors can allow sample fragments (to which the adaptors have been coupled) to be captured by, adhered to, or coupled to a substrate. Such capture allows simplified washing and handling of the fragments, and allows automation of all or part of the method.

Properties of zinc fingers, zinc finger motifs, and their interactions, are described by Nardelli et al., *Zinc finger-DNA recognition: analysis of base specificity by site-directed mutagenesis*. Nucleic Acids Res, 20(16):4137–44 (1992), Jamieson et al., *In vitro selection of zinc fingers with altered DNA-binding specificity*. Biochemistry, 33(19):5689–95 (1994), Chandrasegaran, S. and J. Smith, *Chimeric restriction enzymes: what is next?* Biol Chem, 380(7–8):841–8 (1999), and Smith et al., *A detailed study of the substrate specificity of a chimeric restriction enzyme* Nucleic Acids Res, 27(2):674–81 (1999).

Capturing sample fragments on a substrate may be accomplished in several ways. In one embodiment, capture docks are adhered or coupled to the substrate. Capture docks are compounds or moieties that mediate adherence of a sample fragment by binding to, or interacting with, a capture tag on the fragment. Capture docks immobilized on a substrate allow capture of the fragment on the substrate. Such capture provides a convenient means of washing away reaction components that might interfere with subsequent steps.

Substrates for use in the disclosed method can include any solid material to which components of the assay can be adhered or coupled. Examples of substrates include, but are not limited to, materials such as acrylamide, cellulose, nitrocellulose, glass, silicon, polystyrene, polyethylene vinyl acetate, polypropylene, polymethacrylate, polyethylene, polyethylene oxide, polysilicates, polycarbonates, teflon, fluorocarbons, nylon, silicon rubber, polyanhydrides, polyglycolic acid, polylactic acid, polyorthoesters, polypropylfumerate, collagen, glycosaminoglycans, and polyamino acids. Substrates can have any useful form including thin films or membranes, beads, bottles, dishes, fibers, woven fibers, shaped polymers, particles and microparticles. Preferred forms of substrates are plates and beads. The most preferred form of beads are magnetic beads.

In one embodiment, the capture dock is an oligonucleotide. Methods for immobilizing and coupling oligonucleotides to substrates are well established. For example, suitable attachment methods are described by Pease et al., *Proc. Natl. Acad. Sci. USA* 91(11):5022–5026 (1994), and Khrapko et al., *Mol Biol (Mosk) (USSR)* 25:718–730 (1991). A method for immobilization of 3'1-amine oligonucleotides on casein-coated slides is described by Stimpson et al., *Proc. Natl. Acad Sci. USA* 92:6379–6383 (1995). A preferred method of attaching oligonucleotides to solid-state substrates is described by Guo et al., *Nucleic Acids Res.* 22:5456–5465 (1994).

In another embodiment, the capture dock is the anti-hybrid antibody. Methods for immobilizing antibodies to substrates are well established. Immobilization can be accomplished by attachment, for example, to aminated surfaces, carboxylated surfaces or hydroxylated surfaces using standard immobilization chemistries. Examples of attachment, agents are cyanogen bromide, succinimide, aldehydes, tosyl chloride, avidin-biotin, photocrosslinkable agents, epoxides and maleimides. A preferred attachment agent is glutaraldehyde. These and other attachment agents, as well as methods for their use in attachment, are described in *Protein immobilization: fundamentals and applications*, Richard F. Taylor, ed. (M. Dekker, New York, 1991), Johnstone and Thorpe, *Immunochemistry In Practice* (Blackwell Scientific Publications, Oxford, England, 1987) pages 209–216 and 241–242, and *Immobilized Affinity Ligands*, Craig T. Hermanson et al., eds. (Academic Press, New York, 1992). Antibodies can be attached to a substrate by chemically cross-linking a free amino group on the antibody to reactive side groups present within the substrate. For example, antibodies may be chemically cross-linked to a substrate that contains free amino or carboxyl groups using glutaraldehyde or carbodiimides as cross-linker agents. In this method, aqueous solutions containing free antibodies are incubated with the solid-state substrate in the presence of glutaraldehyde or carbodiimide. For crosslinking with glutaraldehyde the reactants can be incubated with 2% glutaraldehyde by volume in a buffered solution such as 0.1 M sodium cacodylate at pH 7.4. Other standard immobilization chemistries are known by those of skill in the art.

Sorting Tags

A sorting tag is any compound that can be used to sort or separate compounds or complexes having the sorting tag from those that do not. In general, all capture tags can be sorting tags. Sorting tags also include compounds and moieties that can be detected and which can mediate the sorting of tagged components. Such forms of sorting tags are generally not also capture tags. For example, a fluorescent moiety can allow sorting of components tagged with the moiety from those that are not (or those with a different tag). However, such a fluorescent moiety does not necessarily have a suitable capture dock with which it can interact and be captured. Preferably, a sorting tag is a label, such as a fluorescent label, that can mediate sorting.

Amplification Target Circle

An amplification target circle (ATC) is a circular single-stranded DNA molecule, generally containing between 40 to 1000 nucleotides, preferably between about 50 to 150 nucleotides, and most preferably between about 50 to 100 nucleotides. Portions of ATCs have specific functions making the ATC useful for rolling circle amplification (RCA). These portions are referred to as the primer complement portion and the reporter tag portions. The primer complement portion and the reporter tag portion are required elements of an amplification target circle. Those segments of the ATC that do not correspond to a specific portion of the ATC can be arbitrarily chosen sequences. It is preferred that ATCs do not have any sequences that are self-complementary. It is considered that this condition is met if there are no complementary regions greater than six nucleotides long without a mismatch or gap.

An amplification target circle, when replicated, gives rise to a long DNA molecule containing multiple repeats of sequences complementary to the amplification target circle. This long DNA molecule is referred to herein as tandem sequences DNA (TS-DNA). TS-DNA contains sequences complementary to the primer complement portion and the reporter tag portions. These sequences in the TS-DNA are referred to as primer sequences (which match the sequence of the rolling circle replication primer) and reporter tags. Amplification target circles and their use are further described in U.S. Pat. No. 5,854,033.

Method

The disclosed method involves the following basic steps. A nucleic acid sample is incubated with one or more nucleic acid cleaving reagents, preferably restriction endonucleases, that results in a set of DNA fragments cleaved at particular sites. The sample is then mixed with one or more offset adaptors, each of which has a recognition sequence for a nucleic acid cleaving reagent that cleaves at a site offset from the recognition sequence. The offset adaptors are then covalently coupled, preferably by ligation, onto the DNA fragments. The offset adapters should have ends compatible with the ends of the nucleic acid fragments.

The nucleic acid sample is incubated with one or more nucleic acid cleaving reagents, preferably restriction endonucleases, such that a set of DNA fragments having sticky ends with a variety of sequences is generated. Preferred for this purpose is the use of a single Type IIS restriction endonuclease having an offset cleavage site. Since such Type IIS restriction endonucleases cleave at a site different from the recognition sequence, this results in a set of DNA fragments having sticky ends with a variety of sequences. A similar effect can be obtained by digesting the nucleic acid sample with a mixture of restriction endonucleases or other nucleic acid cleaving reagents which cleave at their recognition site.

For a four base sticky end, there are 256 possible sequences. The general formula is $N=4^X$ where $X$ is the length of the sticky end and $N$ is the number of possible sequences. In a sufficiently complex nucleic acid sample, all of these sequences will be represented in the ends of the set of DNA fragments. The nucleic acid sample is also divided into aliquots (referred to as index samples); preferably as many aliquots as there are sticky end sequences (that is, $N=4^X$ aliquots). Where multiple restriction endonucleases are used, the nucleic acid sample is preferably divided into index samples before digestion. Where a single restriction endonuclease is used, the nucleic acid sample is preferably divided into index samples following digestion. Each index sample is then mixed with a different adaptor-indexer, each of which has a sticky end compatible with one of the possible sticky ends on the DNA fragments in that index sample. The adaptor-indexer are then coupled onto compatible DNA fragments. This results in the formation of binary sequence tags. The binary sequence tags have adaptors ligated to each end. The binary sequence tags can then be amplified, if desired, using any suitable method, such as PCR. Sequences in the adaptors can be used as primer binding sites for this amplification.

The binary sequence tags call then be analyzed. Preferably, the binary sequence tags are hybridized with ligator-detectors. One portion of each ligator-detector matches or is complementary to all or part of sequence including, and adjacent to, the sticky end of at least one of the adaptor-indexers. Preferably, the ligator-detector has sequence matching or complementary to one of the possible sticky end sequences generated by digestion with the restriction enzymes. The ligator-detector can also be complementary to nucleotides in the recognition sequence of the restriction enzymes if restriction enzymes that cleave in their recognition sequence are used. Ligator-detectors can also have sequence matching or complementary to common sequences in the adaptor-indexers. In this case, the appropriate ligator-detector is used with each of the index samples. That is, the ligator-detector oligonucleotide used in each index sample matches or is complementary to sequence, including sticky end sequence, in the adaptor-indexer sequence used in that index sample. Alternatively, the ligator-detector can have sequence matching or complementary to sequence of the nucleic acid fragment (to which an adaptor-indexer has been coupled) adjacent to the sticky end sequence and on opposite the side of the fragment from the adaptor-indexer (that is, the offset adaptor side of the binary sequence tag).

Each index sample then can be mixed with detector probes and the probes are coupled to the ligator-detectors. Preferably, the set of probes used include every possible sequence of a given length (for example, every possible six base sequence). The detector probes can be immobilized in an array.

The ends of the detector probes and the ligator-detectors are coupled together only if the probe hybridizes adjacent to the end of the ligator-adaptor. Thus, a ligator-detector is coupled to a detector probe only when a sequence complementary to the probe is present immediately adjacent to the region in a binary sequence tag derived from the original sample to which the end of the ligator-detector hybridizes (preferably the sticky end sequences).

Binary sequence tag will result in an association of a ligator-detector (and an adaptor-indexer and offset adaptor) with a detector probe. This association will be detected through a signal generated from one or several of the associated components. In a preferred form of the disclosed method, the set of detector probes (if multiple sets are used) in which the signal for a given fragment is determined by the sequence of the original sticky end sequence (or recognition sequence). Each different sticky end or recognition sequence is processed in a separate index sample; a separate set of detector probes is used for each index sample or derivative index sample. The probe in the set of probes to which the signal for a given fragment is associated and detected is determined by the sequence in the binary sequence tag adjacent to the sticky end sequence (or recognition sequence) since the detector probe must hybridize to this sequence in order to be coupled to the ligator-detector hybridized to the binary sequence tag. A complex nucleic acid sample will produce a unique pattern of signals in the probe sets. It is this pattern that allows unique cataloging of nucleic acid samples and sensitive and powerful comparisons of the patterns of signals produced from different nucleic acid samples.

The set of detector probes, and particular probe in the set, in which a signal is associated identifies the sequence of the sticky end of the DNA fragment that gave rise to the signal and of the sequence adjacent to the sticky end. This is a ten base sequence when a four base sticky end and six base probes are used. The set of detector probes identifies the sticky end sequence (the four bases) because each set of detector probes used a different adaptor-indexer having a different sticky end sequence. The particular probe identifies the sequence adjacent to the sticky end (the six bases) because each probe has a different probe with a different sequence. Only the probe with sequence complementary to the adjacent sequence will hybridize and thus become associated with a signal.

The information generated is similar when probe arrays are used. The array (if multiple arrays are used) in which the signal for a given fragment is detected is determined by the sequence of the original sticky end sequence (or recognition sequence). Each different sticky end or recognition sequence is processed in a separate index sample; a separate array is used for each index sample or derivative index sample. The location in the array in which the signal for a given fragment is detected is determined by the sequence in the binary sequence tag adjacent to the sticky end sequence (or recognition sequence) since the probe must hybridize to this sequence in order to be coupled to the ligator-detector hybridized to the binary sequence tag. A complex nucleic acid sample will produce a unique pattern of signals on the arrays.

The array, and location in the array, where a DNA fragment generates a signal identifies the sequence of the sticky end of the DNA fragment and of the sequence adjacent to the sticky end. This is a ten base sequence when a four base sticky end and six base probes are used. The array identifies the sticky end sequence (the four bases) because each array used a different adaptor-indexer having a different sticky end sequence. The location in the array identifies the sequence adjacent to the sticky end (the six bases) because each location in the array has a different probe with a different sequence. Only the probe with sequence complementary to the adjacent sequence will hybridize and thus become associated with a signal.

The disclosed method is performed using one or more nucleic acid cleaving reagents that cleave at a site offset from their recognition sequence. Preferred nucleic acid cleaving reagents for use in the disclosed method are Type IIS restriction endonucleases, which are enzymes that cleave DNA at locations outside of (or offset from) the recognition site and which generate sticky ends. Examples of Type IIS restriction endonucleases are FokI, BbvI, HgaI, BspMI and SfaNI.

Nucleic acid cleaving reagents for use in the disclosed method produce sticky ends encompassing permutations and combinations of the four nucleotides, A, C, G, and T. The larger the number of protruding bases, the greater the number of possible permutations and combinations of terminal nucleotide sequences, and the more specific the indexing is likely to be. For example, a restriction endonuclease such as FokI, which releases fragments with four base, 5'-protruding sticky ends, will generate fragments having $4^4$ or 256 possible protruding tetranucleotide ends. The length of the recognition sequence, the length of the sticky end generated, and the length of the probes used together determine the number of data bins (that is, probe identities) into which the binary sequence tag are sorted. By using sticky ends and detector probes of sufficient length, the sorting of fragments can be matched to the complexity of the sample being analyzed.

The use of a comprehensive panel of adaptor-indexers provides a means for attaching specific functional modifications to selected subsets of a complex mixture of nucleic acid fragments and identifying the molecules so modified. Such a defined subset of molecules may be further resolved by additional cleavage and indexing, or by any of the established techniques such as cloning, PCR amplification, or gel electrophoresis. Individual members of the class may be distinguished by identifying characteristics such as length, sequence, or restriction endonuclease maps. The sequence of the sticky ends of the adaptor-indexers provides a means of indexing a large number of nucleic acid fragments.

Detector probes of different sequence can be immobilized at different locations on a probe array. In this way, the sequence of the probes on the probe array and the sequence of the binary sequence tags determine where on the array ligator-detectors become coupled. The presence, amount, presence and amount, or absence of ligator-detector at different locations in the probe arrays thus forms a pattern of signals that provides a signature or fingerprint of the binary sequence tags, and thus of the nucleic acid sample based on the presence or absence of specific nucleic acid sequences in the sample. For this reason, cataloging of this pattern of signals (that is, the pattern of the presence, amount, presence and amount, or absence of ligator-detectors) is an embodiment of the disclosed method that is of particular interest. As discussed elsewhere herein, the probability of probe mismatch can be used to create more complex catalogs based on differential hybridization of particular fragments to different detector probes.

Catalogs can be made up of, or be referred to, as, for example, a pattern of ligator-detectors on probe arrays, a pattern of the presence of ligator-detectors on probe arrays, a catalog of binary sequence tags, a catalog of nucleic acid fragments in a sample, or a catalog of nucleic acid sequences in a sample. The information in the catalog is preferably in the form of positional information (that is, location in the detector array) or, more preferably, in the form of sequences. Preferred sequence information for catalogs include sequences of detector probes to which a ligator-detector was coupled and sequences of nucleic acid fragments present in the sample (derived from the locations in the detector array where ligator-detectors were coupled). Catalogs can also contain or be made up of other information derived from the information generated in the disclosed method, and can be combined with information obtained or generated from any other source. The informational nature of catalogs produced using the disclosed method lends itself to combination and/or analysis using known bioinformatics systems and methods.

Such catalogs of nucleic acid samples can be compared to a similar catalog derived from any other sample to detect similarities and differences in the samples (which is indicative of similarities and differences in the nucleic acids in the samples). For example, a catalog of a first nucleic acid sample can be compared to a catalog of a sample from the same type of organism as the first nucleic acid sample, a sample from the same type of tissue as the first nucleic acid sample, a sample from the same organism as the first nucleic acid sample, a sample obtained from the same source but at time different from that of the first nucleic acid sample, a sample from an organism different from that of the first nucleic acid sample, a sample from a type of tissue different from that of the first nucleic acid sample, a sample from a strain of organism different from that of the first nucleic acid sample, a sample from a species of organism different from that of the first nucleic acid sample, or a sample from a type of organism different from that of the first nucleic acid sample.

The same type of tissue is tissue of the same type such as liver tissue, muscle tissue, or skin (which may be from the same or a different organism or type of organism). The same organism refers to the same individual, animal, or cell. For example, two samples taken from a patient are from the same organism. The same source is similar but broader, referring to samples from, for example, the same organism, the same tissue from the same organism, the same cDNA, or the same cDNA library. Samples from the same source that are to be compared can be collected at different times (thus allowing for potential changes over time to be detected). This is especially useful when the effect of a treatment or change in condition is to be assessed. Samples from the same source that have undergone different treatments can also be collected and compared using the disclosed method. A different organism refers to a different individual organism, such as a different patient, a different individual animal. Different organism includes a different organism of the same type or organisms of different types. A different type of organism refers to organisms of different types such as a dog and cat, a human and a mouse, or E. coli and Salmonella. A different type of tissue refers to tissues of different types such as liver and kidney, or skin and brain. A different strain or species of organism refers to organisms differing in their species or strain designation as those terms are understood in the art.

Offset adaptors and adaptor-indexers are preferably coupled to nucleic acid fragments in their double-stranded form since ligation will be more efficient. However, the two strands of an offset adaptor or adaptor-indexer can be used separately in the disclosed method. For example, the two strands of the offset adaptor or adaptor-indexer can be coupled to a nucleic acid fragment separately. Thus, the steps of mixing and coupling offset adaptors or adaptor-indexers to nucleic acid fragments encompasses both mixing and coupling of double-stranded forms of offset adaptor or adaptor-indexer and separately mixing and coupling the strands of offset adaptors or adaptor-indexers.

When a first offset adaptor strand is coupled to a nucleic acid fragment, the double-stranded recognition site for cleavage can be formed other than by covalently coupling the second offset adaptor strand to the nucleic acid fragment. For example, the second offset adaptor strand can be hybridized to the first offset adaptor strand, but not coupled to the nucleic acid fragment. The hybrid need only stay together through cleavage of the fragment with second nucleic acid cleaving reagent. The offset adaptor region of the nucleic acid fragment need not be fully double-stranded so long as the recognition site is functional. Alternatively, the other strand of the offset adaptor can be formed by filling in the single-stranded portion of the first offset adaptor coupled to the nucleic acid fragment.

When a first adaptor-indexer strand is coupled to a nucleic acid fragment, the second strand need not be used or added. Coupling of the first adaptor-indexer strand alone can complete the formation of one strand of a binary sequence tag. This is all that is required for many forms of manipulation and analysis of binary sequence tags. A coupled, double-stranded adaptor-indexer can be formed other than by covalently coupling the second adaptor-indexer strand to the nucleic acid fragment. For example, the other strand of the adaptor-indexer can be formed by filling in the single-stranded portion of the first adaptor-indexer coupled to the nucleic acid fragment. As with the second offset adaptor strand, the second adaptor-indexer strand can be hybridized to the first adaptor-indexer strand without coupling it to the nucleic acid fragment.

When comparing catalogs of binary sequence tags obtained from related samples, it is possible to identify the presence of a subset of correlated pairs. Binary sequence tags produced using the disclosed method generally occur in correlated pairs, except in a few cases where the initial cleavage site occurs near the terminus of a DNA substrate. Correlated pairs of binary sequence tags are the two tags that result from the initial cleavage at a particular site. An offset adaptor is coupled to each end of the cleavage site, eventually resulting in the two correlated binary sequence tags.

cDNA generated from long mRNA molecules is likely to generate a complex pattern of binary sequence tags. On the other hand, shorter cDNAs are likely to generate relatively fewer binary sequence tags. If a small concentration of a di-deoxy nucleotide triphosphate is included in the first strand cDNA synthesis reaction, first strand synthesis will result in a distribution of strands with a relatively lower representation of longer molecules. In the specific case where ddCTP is used as a terminator, the probability P of chain extension at every position where C is present is given by:

$$P=([dCTP])/([dCTP]+q[ddCTP]),$$

where q is the incorporation efficiency of ddCTP relative to dCTP. The probability of extension for a chain containing C at n positions is $P^n$.

By generating the second strand with random primers, a skewed distribution of double-stranded DNA fragments is preserved in which sequences near the 3'-end of the cDNA are over-represented. As a result, binary sequence tags originating from sequences near the 3' end will also be over-represented relative to binary sequence tags originating from sequences closer to the 5' end. Among the binary sequence tags generated from such a cDNA, it will be possible to identify a pattern of correlated pairs, where the abundance (that is, the signal intensity) of each correlated pair is nearly the same. Different correlated pairs arise from cleavage sites distant from, each other and can be ordered according to their abundance. For genomes of known sequence, the data obtained from several assays using cDNAs with a skewed 3'-end representation, can be used to generate large datasets of correlated tags and the corresponding intensity signal gradients. These gradients can be calibrated with the distance of each binary sequence tag from the 3'-end of the cDNA. Signal gradients of correlated tags can thus serve as calibrators in other assays involving the analysis of mRNA transcripts from genomes of unknown sequence.

This can be illustrated with the following example of a catalog with three candidate correlated tags as might be obtained from an experiment performed in an organism whose genomic sequence is known.

| Tag address | Test/control ratio | Test level | Control level |
|---|---|---|---|
| A | 15.5 | 322 | 21 |
| B | 14.8 | 319 | 22 |
| C | 16.1 | 244 | 15 |
| D | 15.3 | 239 | 16 |
| F | 14.9 | 171 | 11 |
| G | 16.0 | 189 | 12 |

In this example, the top pair of correlated tags is located near the 3'-end of a unique cDNA, where the cDNA has been up-regulated by a factor of approximately 15 in the test sample. The other two pairs of tags have in common a very similar test/control expression ratio, and occur at positions of increasing distance from the 3'-end of the cDNA. The absolute levels of expression also occur as binary pairs, and show a correlation with the distance in nucleotides relative to the 3'-end of the cDNA. That is, the absolute level of the tags goes down the further source sequence of the tag is from the 3' end. The level of both binary sequence tags in a pair go down together, in a correlated fashion (thus, keeping their ratio the same).

If a similar assay were performed in an organism whose genome has not been sequenced, correlated binary sequence tags that share approximately the same expression ratio, and that display graded levels of absolute expression values, may be used to infer the possible order of the binary sequence tags derived from a specific cDNA. Repeating the assay using cDNA generating in the presence of a different level of the same ddNTP, or the same level of a different ddNTP, will generate additional data that can confirm or strengthen the identification, ordering, and separation distance of the putative correlated binary sequence tags believed to be derived from the same gene. The analysis of correlated binary sequence tags can be simplified by using anchored primers. As described elsewhere herein, anchored primers can be used to produce a less complex nucleic acid sample. The reduced complexity will result in fewer tags to be analyzed. It should also be noted that alternative splicing events may lead to different distance maps for correlated binary sequence tags derived from genes that have such splicing patterns.

Since correlated tags are derived from adjacent sequences in the original nucleic acid molecule, once correlated pairs are identified, their sequences, when put together, represent a longer sequence in the original nucleic acid fragment. For example, when the disclosed method is performed using MboI and FokI, the information content of the correlated binary tags would be 24 (4+6+4+6+4) nucleotides. These longer sequences can be added to the catalog of tags.

The presence, amount, presence and amount, or absence of ligator-detectors coupled to detector probes can be accomplished by detection of labels incorporated into, coupled to, or associated with the ligator-detectors. Alternatively, the ligator-detectors can be detected based on detection of their sequence. These detections are generally referred to as direct detection of coupling of ligator-detectors. Any of the numerous sequence-specific detection techniques can be used for this purpose, including, for example, hybridization of labeled probes. The presence, amount, presence and amount, or absence of ligator detectors can also be detected by generating a signal mediated by the ligator-detector. Use of the ligator-detector as a primer for rolling circle replication, described below, is a preferred example of this. The presence, amount, presence and amount, or absence of ligator detectors can also be detected by detecting the detector probe to which the ligator-detector is coupled, the adaptor-indexer associated with the coupled ligator-detector, the offset adaptor associated with the coupled ligator-detector, or a combination. These detections are generally referred to as indirect detection of coupling of ligator-detectors.

The signal to be detected for the binary sequence tags can be increased by nucleic acid amplification during the method. It is preferred either that the binary sequence tags be amplified or that the ligator-detectors that have been coupled to detector probes be amplified or mediate amplification of another nucleic acid. In the first case, the binary sequence tags can be amplified using any suitable method. These include polymerase chain reaction (PCR), ligase chain reaction (LCR), self-sustained sequence replication (3SR), nucleic acid sequence based amplification (NASBA), strand displacement amplification (SDA), amplification with Qβ replicase, and rolling circle amplification (RCA) (Birkenmeyer and Mushahwar, *J. Virological Methods,* 35:117–126 (1991); Landegren, *Trends Genetics,* 9:199–202 (1993); Lizardi et al., *Nature Genetics* 19(3):225–232 (1998)). In the case of ligator-detector amplification, a preferred form of amplification is rolling circle amplification of a single-stranded circular DNA molecule primed by the ligator-detector. In this way, a long tandem repeat of the DNA circle is generated with the amplified strand anchored to the detector array via the ligator-detector. This technique of amplification is described in PCT application WO 97/19193. If the ligator-detector is used as a rolling circle replication primer, there is no need to incorporate a label in the ligator-detector since the amplified DNA can be detected (either directly or via an incorporated label).

Amplification of the binary sequence tags is facilitated by the presence of offset adaptor and adaptor-indexer sequence at the ends of the binary sequence tags. For example, the offset adaptor sequences and adaptor-indexer sequences can be used for amplification of primer sequences. The offset adaptor and adaptor-indexer sequences can also be used to circularize the binary sequence tags for subsequent amplification by rolling circle replication. Rolling circle amplification is described in U.S. Pat. No. 5,854,033 and PCT application WO 97/19193.

In another embodiment, the strands of binary sequence tags can be separated prior to hybridization to the ligator-detectors. Such strand separation can improve the efficiency of ligator-detector hybridization. This separation can be accomplished using any suitable technique. Strand separation is preferably accomplished by including a capture tag or sorting tag on one of the strands of the offset adaptors or adaptor-indexers. Such a capture tag can then be used to immobilize one strand of the binary sequence tags while the other strands are washed away. Either the immobilized or washed strand can be carried forward in the method. A sorting tag can allow separation of the strands by a sorting technique.

In another embodiment, the concentrations of the various nucleic acid fragments in the index samples are normalized. Preferably, the concentrations of binary sequence tags are normalized. Normalization can be performed either before or after any amplification step that may be used. A preferred technique for fragment normalization involves immobilizing one strand of the nucleic acid fragments (preferably the binary sequence tags), denaturing the nucleic acid fragments, renaturing the nucleic acid fragments for a time greater than the $c_0t_{1/2}$ for abundant nucleic acid fragments and less than the $c_0t_{1/2}$ for rare nucleic acid fragments, and collecting the un-renatured nucleic acid fragments.

A number of varied probe sets and arrays are known in the art and can be used with the disclosed method. Terstappen et al. (Tibbe et al., *Optical tracking and detection of immunomagnetically selected and aligned cells* Nat Biotechnol, 17(12):1210–3 (1999); U.S. Pat. No. 5,985,153 (Dolan and Terstappen, *Magnetic separation apparatus and methods employing an internal magnetic capture gradient and an external transport force*); U.S. Pat. No. 5,993,665 (Terstappen and Liberti, *Quantitative cell analysis methods employing magnetic separation*); U.S. Pat. No. 6,013,188 (Terstappen and Liberti, *Methods for biological substance analysis employing internal magnetic gradients separation and an externally-applied transport force*)) have demonstrated immunomagnetically selected and fluorescently labeled probes for detection of cells of interest. In their technique the cells are labeled using immunospecific binding probes and the resulting labeled cells are induced to move into detector range by an externally applied magnetic field. Lithographic processing of one wall of the sample vessel leads to the improvement of locating the tagged cells along well determined spatial patterns.

Thorp et al. (Napier et al., *Probing biomolecule recognition with electron transfer: electrochemical sensors for DNA hybridization*. Bioconjug Chem, 8(6):906–13 (1997); U.S. Pat. No. 5,968,745 (Thorp et al., *Polymer-electrodes for detecting nucleic acid hybridization and method of use thereof*); U.S. Pat. No. 5,871,918 (Thorp et al., *Electrochemical detection of nucleic acid hybridization*); WO 99/64847 (Welch, *Electrochemical probes for detection of molecular interactions and drug discovery*)) have developed an electrochemical detection method. Their method directly detects target nucleic acids without sample amplification or use of fluorescent labels. Detection is accomplished by following the oxidation-reduction cycle of $Ru(bpy)_3^{2+}$ by electrochemical measurement. The measurement elements have synthetically prepared oligonucleotide probes attached to electrodes, the electrodes have been fabricated into a variety of formats including biochips, microtiter plates and hand-held devices.

Spectral labeling coupled with a counting technique, such as flow cytometry, has been exploited for analysis of DNA samples (U.S. Pat. No. 5,736,330 (Fulton, *Methods and compositions for flow cytometric determination of DNA sequences*); WO 99/19515 (Phipps et al., *Precision fluorescently dyed particles and methods of making and using same*); WO 99/37814 (Chandler and Chandler, *Microparticles with multiple fluorescent signals*)). In such analyses, micron scale beads are color coded according to the probes attached to their surface, targets are labeled with an analytical fluorescent tag, and the coincidence events containing the bead color and the analytical color are counted. In this manner a probe array of many colors can be read out very quickly and easily.

In another technique utilizing microspheres, Walt et al. (Walt, *Techview: molecular biology. Bead-based fiber-optic arrays* Science 287(5452):451–2 (2000); WO 98/50782 (Ferguson et al., *Fiber optic biosensor for selectively detecting oligonucleotide species in a mixed fluid sample*); U.S. Pat. No. 6,023,540 (Walt and Michael, *Fiber optic sensor with encoded microspheres*); Michael et al., *Randomly ordered addressable high-density optical sensor arrays*. Anal Chem, 70(7):1242–8 (1988)) have developed a system where the probes are attached to the microspheres and the microspheres subsequently self assemble in a random spatial pattern into the distal end of a fiber optic array. The "optical bar code" signature of each microsphere provides the identity of the attached probe, and signal of the labeled target indicates the concentration of the target.

One of the ways in which sequence tags identified using the disclosed method can be used is to create arrays of oligomers based on the sequence tags. Thus, new oligomers, with appropriate coupling chemistry and spacers, are synthesized which correspond to the sequence tag. These tags are arrayed and coupled appropriately on a microarray slide to yield a new microarray with expressed sequence tag probes for the organism of interest. Such arrays can be used in any of a variety of methods that involve arrays of oligonucleotides, including the disclosed method. In particular, the array can be used to detect similarities and differences between sequences present in the original sample and any future sample.

If genomic sequence information is available, a BLAST search using sequence derived from binary sequence tags may indicate the presence of a promoter if the sequence lies 5' of a characterized gene. In silico analysis of predicted methylation sites should facilitate such assumptions. If genomic sequence is unavailable, the sequence tag can serve as a starting point to facilitate characterization of previously undefined genomic DNA regions of interest.

Modification Assisted Analysis of Binary Sequence Tags (MAABST)

Modification assisted analysis of binary sequence tags (MAABST) is a form of BEST that assesses modification of sequences in nucleic acid molecules by detecting differential cleavage based on the presence or absence of modification in the molecules. For example, a site that is methylated in a nucleic acid molecule will not be cut by a restriction enzyme that is sensitive to methylation at that site. A restriction enzyme that is insensitive to methylation will cleave at that site, thus producing a different pattern of sequence tags. Comparison of the results with different samples of nucleic acids can establish differences in the modification levels or patterns in the different samples. As used herein, a nucleic acid cleaving reagent or restriction enzyme that is sensitive to modification in its recognition site is a nucleic acid cleaving reagent or restriction enzyme that will either cleave only when the site is unmodified or will cleave only when the site is modified (that is, the nucleic acid cleaving reagent or restriction enzyme requires a particular modification state for cleavage). A nucleic acid cleaving reagent or restriction enzyme that is insensitive to modification in its recognition site is a nucleic acid cleaving reagent or restriction enzyme that will cleave regardless of whether the site is modified or unmodified.

MAABST is useful for assessing the state, level, and condition of modifications in nucleic acid molecules. Many nucleic acid modifications are known that have biological effects and significance. Methylation, for example, is a universal mechanism for regulating gene expression in animals and plants (Bird and Wolffe, *Methylation-induced repression-belts, braces, and chromatin*, Cell 99:451–454 (1999); Finnegan et al., *DNA Methylation in Plants*, Annual Rev Physiol 49:223–247 (1998); Bird, *DNA Methylation de Novo*, Science 286:2287–2288 (1999)). Understanding the physiological consequences of methylation has utility in a number of fields. It is well documented that methylation of promoter regions can repress transcription, both in vitro and in vivo (Baylin et al., *Alterations in DNA methylation: a fundamental aspect of neoplasia*, Adv Cancer Res 72:141–96 (1998)). For instance, the promoters of several genes implicated in neoplasia and tumor suppression are subject to hypermethylation (Melki et al., *Concurrent DNA hypermethylation of multiple genes in acute myeloid leukemia*, Cancer Res 59(15):3730–40 (1999)). Methylation also performs important functions in plant development and flowering.

The use of differential methylation to study gene function traditionally required prior knowledge of DNA sequences subject to methylation, obtained only after substantial effort to clone, sequence and verify the methylation sensitivity of the region of interest. MAABST expedites the identification of differentially methylated sequences by, in its preferred forms, combining the power of high throughput microarray technology and in silico analysis with the sensitivity and quantitation of differential display.

MAABST has several advantages over other methods currently used to identify promoters on a genomic scale. Current approaches to identify promoter and other regulatory elements in a high throughput manner include: in silico analysis of nucleotide sequence for transcription factor binding sites, β-lactamase insertion (Whitney et al, *A genome-wide functional assay of signal transduction in living mammalian cells*, Nat Biotechnol 16(13):1329–33 (1998)). COBRA (Xiong and Laird, *COBRA: a sensitive and quantitative DNA methylation assay*, Nuc Acid Res 25(12):2532–2534 (1997)), and restriction landmark genomic scanning (Costell et al., *aberrant CpG-island methylation has non-random and tumour-type-specific patterns*, Nature Genetics 25:132–138 (2000)).

Other forms of modification are indicative of certain types of DNA damage caused by particular agents. These include alkylation, dimerization, derivatization, depurination, or ADP-ribosylation. Examples of modifications and their source are described in Lodovici et al., Levels of 8-hydroxydeoxyguanosine as a marker of DNA damage in human leukocytes, Free Radic Biol Med 28(1): 13–7 (2000); Maehira et al., Alterations of protein kinase C, 8-hydroxydeoxyguanosine, and K-ras oncogene in rat lungs exposed to passive smoking Clin Chim Acta 289(1–2): 133–44 (1999); Gamboa Da Costa et al., Characterization of the Major DNA Adduct Formed by alpha-Hydroxy-N-desmethyltamoxifen in Vitro and in Vivo, Chem Res Toxicol 13(3):200–207 (2000); Phillips et al., Methods of DNA adduct determination and their application to testing compounds for genotoxicity, Environ Mol Mutagen 35(3): 222–233 (2000); Airoldi et al., Carcinogen-DNA adducts as tools in risk assessment, Adv Exp Med Biol 472:231–40 (1999); Purewal et al., Association between acetylator genotype and 2-amino-1-methyl-6-phenylimidazo[4,5–b] pyridine (PhIP) DNA adduct formation in colon and prostate of inbred Fischer 344 and Wistar Kyoto rats, Cancer Lett 149(1–2):53–60 (2000).

MAABST uses the same basic steps as BEST and includes cleavage with a nucleic acid cleaving reagent and coupling of an offset adaptor to the nucleic acid fragments. The difference is that MAABST uses a nucleic acid cleaving reagent that is sensitive to modification of its recognition site. Thus, the nucleic acid cleaving reagent will either not cleave at a site that is modified or cleave only at a site that is modified. In nucleic acid fragments that have a modification at the recognition site, the fragment will not be cleaved by the nucleic acid cleavage reagent and no offset adaptor will be added to the end.

Uncleaved nucleic acid fragments can be culled from the procedure in a number of ways. For example, if the nucleic acid fragments are to be amplified following addition of the offset adaptors, amplification can be made dependent on the presence of an offset adaptor on the end. This can be accomplished, for example by using a PCR primer complementary to sequence in the offset adaptor. The uncleaved nucleic acid fragments can also be culled by, for example, including a capture tag, sorting tag, or label in the offset adaptor. By capturing or sorting the fragments based on the presence or absence of the capture or sorting tag, only those fragments containing an offset adaptor are carried forward in the procedure.

If a label is associated with the offset adaptor, all of the fragments can be carried forward in the procedure but only those having an offset adaptor (and thus a label) will produce a detectable signal (in this scenario, the label on the offset adaptor would have to be detected in association with a detector probe and/or a ligator-detector). Use of a label in this manner in the offset adaptor can also allow discrimination of cleaved and uncleaved fragments (that is, fragments cleaved or not cleaved by the nucleic acid cleaving reagent). This can be accomplished by detecting coupling of ligator-detectors to detector probes via labels, capture tags, or sorting tags on the detector probes, ligator-detectors, or adaptor-indexers and also detecting the presence, amount, presence and amount, or absence of an offset adaptor on the fragment via its label.

MAABST can also be used to determine how one type of cell or organism influences gene expression or other biological pathways in another type of cell or organism. For example, suppose that a mouse is genetically altered via gene targeting to inactivate a particular methyltransferase gene (there are several known for mouse but for illustration purposes, assume there is only one). Cells of interest (for instance, B cells) are taken from a mouse genetically altered to inactivate the methyl transferase mechanism and mixed with other cells of interest (for instance, T cells) obtained from a normal mouse. The B and T cells are mixed together. The T cell methylation pattern between B cell mixed and non-B cell mixed could then be compared. It can be concluded that the observed changes in methylation occurred within the T cells since the B cells harbored an inactivated methyltransferase.

Using standard differential gene expression techniques, it would be very difficult for many genes, and impossible for others, to distinguish which transcripts originated in the B cells and which transcripts originated in the T cells (since any two cell types will share expression of a number of genes). However, due to the prior genetic alterations, that is, deleting the methyltransferase gene, MAABST allows examination of gene expression in a mixed cell population. An example of MAABST is described in Illustration 7.

Mass Spectroscopy Detection

Mass spectrometry techniques can be utilized for detection in BEST. These techniques include matrix-assisted laser desorption/ionization time-of-flight (MALDI-TOF) mass spectroscopy. Such techniques allow automation and rapid throughput of multiple samples and assays.

Mass spectrometry detection works better with smaller molecules so it is preferable to cut some BEST components prior to, or as part of mass spectrometry detection. A number of methods are contemplated where an oligonucleotide molecule to be detected is cut to a shorter length prior to detection by mass spectrometry. The BEST protocol would proceed as normal and, in the preferred embodiment, the surface that has the hexamer probes attached would be compatible with the source region of a matrix assisted laser desorption ionization, time of flight, mass spectrometer (MALDI-TOF-MS). The resultant fragment of the BEST process for this particular case would look something like:

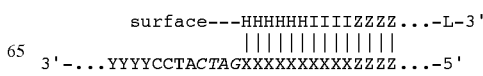

Where:
H are the hexamer probe;
3'-CTAG-5' in lower strand indicates the initial Type II restriction site (MboI);
3'-CCTAC-5' in lower strand indicates the Type IIS restriction site (FokI);
Y are the remainder of the offset adapter;
I are the quadramer from the indexing step;
Z are the remainder of the adapter-indexer;
- are linker, universal bases, mimics or other analogs;
X are complementary bases, not germane;
L is a label.

The bottom strand is SEQ ID NO:8.

For DNA samples of greater than approximately 50 bases the performance of mass spectrometry techniques is reduced. Chemical, biological, physical (thermal), and other cleaving reagents can be used to generate smaller, more optimal, sub-fragments to be analyzed in the mass spectrometer. The degree of fragmentation is somewhat tunable in instruments like the Q-TOF systems (Micromass, US head office at Suite 407N, 100 Cummings Center, Beverly, Mass. 01915-6101, USA.) where one can look at the parent ion, then increase the fragmentation to see the decomposition fragments and thus the sequence; such a technique is contemplated to determine the full sized sub-fragment, and infer the sequence (which is longer sequence information than for the basic BEST method) of the sub-fragment through these known tools. The detectable fragment can be top strand, bottom strand, or both strands depending upon the scheme. The label may be a cleavable mass tag or the strand need not be labeled.

There are several useful cleaving reagents for this purpose. For example, one technique is that of Szybalski (described elsewhere herein) where FokI is used to cut at a fixed distance from an arbitrary, specific, recognition site. This technique can be extended to other restriction enzymes of Type IIS or Type III. This technique can also be used twice, once to trim off the end nearer the surface, once to trim off the end further from the surface; preferably a Type II enzyme would be used to cut the end furthest from the surface.

Use of McrBC (New England Biolabs), can be used to cut at methylcytosine sites adjacent to G/A. The cut site is not well defined (approximately 30 bases) which may be used to advantage to generate the parent as well as the fragmentation set. Metal containing porphyrins attached to oligonucleotides have been shown to cut DNA very near the porphyrin when exposed to light (Texaphyrins, U.S. Pat. No. 5,607, 924). One could denature and use a hybridization texaphryin and light to cleave the remaining strand. Another cleavage technology is that of Dervan (Cartwright et al., *Cleavage of chromatin with methidiumpropyl-EDTA iron(II)*. Proc Natl Acad Sci USA, 80(11):3213–7 (1983); Schultz and Dervan, *Sequence-specific double-strand cleavage of DNA by penta-N-methylpyrrolecarboxamide-EDTA X Fe(II)*. Proc Natl Acad Sci USA, 80(22):6834–7 (1983)). Techniques using photocleavable linkages are described by Olejnik et al. (Olejnik et al., *Photocleavable peptide-DNA conjugates synthesis and applications to DNA analysis using MALDI-MS*. Nucleic Acids Res, 27(23):4626–31 (1999); Olejnik et al., *Photocleavable affinity tags for isolation and detection of biomolecules*. Methods Enzymol, 291:135–54 (1998); Olejnik et al., *Photocleavable aminotag phosphoramidites for 5'-termini DNA/RNA labeling*. Nucleic Acids Res, 26(15): 3572–6 (1998); Olejnik et al., *Photocleavable biotin derivatives: a versatile approach for the isolation of biomolecules*. Proc Natl Acad Sci USA, 92(16):7590–4 (1995)) These linkages can be cleaved using light to release the fragment from the surface, thus providing a more gentle desorption. WO 0004036 describes photocleavable nucleotides and methods for their use.

In one embodiment, a mass label such as peptide nucleic acid (PNA) molecules (Hanvey et al., Science 258:1481–1485 (1992)) of different sequence and molecular weight can be used as labels that bind specifically to sequence in ligator-detectors or adaptor-indexers. Laser desorption of the samples is used to generate MALDI-TOF mass spectra of the PNA labels, which are released into the spectrometer and resolved by mass. The intensity of each PNA label reveals the relative amount of different components (e.g. ligator-detectors or adaptor-indexers. In other words, the PNA spectra generate scalar values that are indirect indicators of the relative abundance of the labeled component at specific locations in an array.

The mass of the fragment itself and/or its fragmentation pattern, generated, for example, by collisionally induced dissociation (CID), can be used to verify that the hexamer was correctly hybridized and will provide additional control/tester ratio information. A preferred instrument for this CID option would make use of a tandem mass spectrometer of the class of a MALDI-qQTOF as described by Loboda et al (Loboda et al. *Design and Performance of a MALDI-OqTOF Mass Spectrometer in 47th ASMS Conference.* 1999. Dallas, Tex.) where the first quadrapole is used to select the mass of interest and the collision cell is used to generate the fragment spectrum. It has been reported by Shaw-Smith et al (Biotechniques, 28:958–964 (2000)) that the subdivision of a cDNA population by indexing (Unrau and Deugau, Gene 145(2):163–9 (1994)) is subject to the generation of redundant subsets due to mismatched ligation of adapters. In the majority of cases, the mismatch ligation involves a single mispaired base. Ligation conditions may be modified, by using thermostable ligases at high temperature, to reduce the frequency of mismatch ligation, but often the conditions that lead to reduction of mismatches also result in reduced ligation efficiency for AT-rich overhangs. One form of the disclosed method provides an alternative to indexing, which may be described as "capture of redundant subsets." Conditions for ligation of restriction enzyme fragments to adapters may be modified for high-yield ligation of perfectly matched sequences, with concurrent ligation of a few sequences with a single base mismatch. This high-yield method results in the generation of redundant subsets, instead of unique subsets. The cDNA fragments present in each redundant subset may then be further analyzed, for example, as follows:

1. A pair of adaptor-indexer-specific oligonucleotides, one of which contains a biotin, are used to amplify the cDNA fragments by PCR. For assays involving a tester and a control sample, one of the primers used to amplify one of these samples will preferably contain one or more additional 5'-terminal bases, in order to make the masses of the control and tester tags easily resolvable by the mass spectrometer.

2. Single stranded amplicons are isolated by binding to streptavidin beads, followed by release of the unbound strand.

3. The single stranded cDNA tags are hybridized with a ligator-detector oligonucleotide, and then contacted with a microarray comprising all hexamers. Ligation is performed in a solution in contact with the array surface, under conditions generating maximum specificity of hexamer base pairing. A different hexamer microarray is used for each of the 256 possible adaptor-indexers.

4. The microarray is washed to remove weakly bound cDNA tags.

5. The microarrays spots are covered with a suitable matrix for performing analysis of DNA by mass spectrometry.

6. Mass analysis is performed using a MALDI source, tandem quadrupole, quadrupole, time-of-flight mass spectrometer by tuning the first quadrupole filter for transmission of a single mass-to-charge. The microarray consists of all possible hexamers; a correctly hybridized cDNA tag bound at a unique address has a single, well defined mass. In addition, for each of the 256 possible adapters, the sequence of the adapter cohesive end is known, and also corresponds to a single mass. Hence, it is possible to determine in advance which precise cDNA mass tag window to use for each of the 4096 array addresses, and for each of the 256 microarrays. For example, there exist a total of 84 possible different mass combinations for the unique cDNA tags that bind to specific addresses on a microarray of 4096 hexamers, using a single adaptor sequence. The general formula is a binomial coefficient of the form:

Combinations=$[(n+r-1)!]/[n!(r-1)!]$.

In this expression "n" is the number of bases in a detector sequence in the microarray, while "r" is the number of possible values for the mass of a base. Resolving for n=6 and r=4, r-=3; $[(6+3)*(6+2)*(6+1)]/3!=9*8*7/6=84$.

The signal measured in the mass spectrometer corresponds to the number of DNA ions that have the mass for which a specific array address has been tuned. Most DNA molecules that are present at an incorrect address will have a single base mismatch, either in the hexamer sequence, or in the adaptor-indexer sequence; all such molecules will have a different mass, and will not be detected. Molecules with two mismatches are most likely to also have a different mass, except in the special case of molecules with two mismatched bases that exactly compensate each other. Such molecules may be scored by collecting a fragmentation pattern in the collision cell of the tandem mass spectrometer their incorrect fragment masses in the fragmentation (see below).

An additional, optional step in the mass spectrometry analysis is fragmentation in the subsequent collision cell—a quadrupole acting as an ion guide and a region of relatively high pressure chemically inert gas—followed by TOF analysis of the DNA fragments. Fragmentation and TOF analysis will resolve the fragments originating from correct adapter-indexer ligation and correct hexamer ligation, from other fragments of equal mass, but different sequence, resulting from possible mutually compensatory mismatches at the adaptor-indexer ligation and the hexamer ligation steps.

Further, photocleavable nucleotides or linkers can be used which will yield a shorter, well defined, fragment from the binary sequence tag upon laser irradiation in the MALDI source. Photocleavable linkers may be used in the attachment of the mass labels wherein the linkage will cleave and release the mass tag when the samples are subjected to the UV source of the MALDI.

Still further, use of uracil rather than thymine in the synthetic adapters (phosphoramidite chemicals available from Glenn Research) may be used in conjunction with uracil-DNA glycosylase, UDG, (available from New England Biolabs) to introduce specific strand breaks which can be designed to release particular fragments upon treatment with UDG. Such strand breaks may be engineered to be offset in the sense and antisense strands such that the complex remains substantially intact near room temperature until subjected to the laser of the MALDI source.

Multiplex detection using mass spectrometry can also be accomplished using sets of mass tags. The mass tags preferably have two key features. First, the tags are used in sets where all the tags in the set have similar properties. The similar properties allow the tags to be separated from other molecules lacking one or more of the properties. Preferably, the tags in a set have the same mass-to-charge ratio (m/z). That is, the tags in a set are isobaric. This allows the tags to be separated precisely from other molecules based on mass-to-charge ratio. The result of the filtering is a huge increase in the signal to noise ratio (s/n) for the system, allowing more sensitive and accurate detection.

Second, all the mass tags in a set can be fragmented, decomposed, reacted, derivatized, or otherwise modified to distinguish the different tags in the set. Preferably, the mass tags are fragmented to yield fragments of similar charge but different mass. This allows each mass tag in a set to be distinguished by the different mass-to-charge rations of the fragments of the tags. This is possible since, although the unfragmented mass tags in a set are isobaric, the fragments of the different mass tags are not.

Differential distribution of mass in the fragments of the mass tags can be accomplished in a number of ways. For example, mass tags of the same nominal structure (for example, peptides having the same amino acid sequence), can be made with different distributions of heavy isotopes, such as deuterium. All mass tags in the set would have the same number of a given heavy isotope, but the distribution of these would differ for different mass tags. Similarly, mass tags of the same general structure (for example, peptides having the same amino acid sequence), can be made with different distributions of modifications, such as methylation, phosphorylation, sulphation, and use of seleno-methionine for methionine. All mass tags in the set would have the same number of a given modification, but the distribution of these would differ for different mass tags. Mass tags of the same nominal composition (for example, made up of the same amino acids), can be made with different ordering of the subunits or components of the signal. All mass tags in the set would have the same number of subunits or components, but the distribution of these would be different for different mass tags. Mass tags having the same nominal composition (for example, made up of the same amino acids), can be made with a labile or scissile bond at a different location in the signal. All mass tags in the set would have the same number and order of subunits or components. Where the labile bond is present between particular subunits or components, the order of subunits or components in the mass tag can be the same except for the subunits or components creating the labile bond. Each of these modes can be combined with one or more of the other modes to produce differential distribution of mass in the fragments of the mass tags. For example, different distributions of heavy isotopes can be used in mass tags where a labile bond is placed in different locations.

The mass tags are preferably detected using mass spectrometry which allows sensitive distinctions between molecules based on their mass-to-charge ratios. The disclosed mass tags can be used as labels for any of the component of the disclosed method. For example, mass labels can be used on ligator-detectors, adaptor-indexers, or offset adaptors. Once the binary sequence tags are immobilized via ligation of the ligator-detector, the mass tag can be detected. Preferably, the mass tags would be dissociated from the labeled component during, or prior to, detection. A set of isobaric mass tags can be used for multiplex labeling and/or detection of many binary sequence tags since the mass tag fragments can be designed to have a large range of masses, with each mass individually distinguishable upon detection.

A preferred form of mass tag detection involves filtering of isobaric mass tags from other molecules based on mass-to-charge ratio, fragmentation of the mass tags to produce fragments having different mass-to-charge ratios, and detection of the different fragments based on their mass-to-charge ratios. The technique is best carried out using a tandem mass spectrometer where the isobaric mass tags are passed through a filtering quadrupole, the mass tags are fragmented in a collisional cell, and the fragments are distinguished and detected in a time-of-flight (TOF) stage. In such an instrument the sample is ionized in the source (for example, in a MALDI) to produce charged ions. It is preferred that the ionization conditions are such that primarily a singly charged parent ion is produced. A first quadrupole, Q0, is operated in radio frequency (RF) mode only and acts as an ion guide for all charged particles. The second quadrupole, Q1, is operated in RF+DC mode to pass only a narrow range of mass-to-charge ratios (that includes the mass-to-charge ratio of the mass tags). This quadrupole selects the mass-to-charge ratio of interest. Quadrupole Q2, surrounded by a collision cell, is operated in RF only mode and acts as ion guide. The collision cell surrounding Q2 will be filled to appropriate pressure with a gas to fracture the input ions by collisionally induced dissociation. The collision gas preferably is chemically inert, but reactive gases can also be used. Preferred molecular systems utilize mass tags that contain scissile bonds, labile bonds, or combinations, such that these bonds will be preferentially fractured in the Q2 collision cell.

Probability Detection

Sequencing by hybridization is known to produce mismatch errors (Lipshutz, *Likelihood DNA sequencing by hybridization*. J Biomol Struct Dyn, 11(3):637–53 (1993)). Database searching for sequence information currently is regular expression based and requires matched "letters" between the database entry and the search sequence. BEST allows replacement of regular expression matching (match versus no-match per base) with a probability function to determine a confidence in the assignment of the identity of a binary sequence tag.

The disclosed method uses ligation to improve the specificity of the hybridization near the ligation site. Despite this improvement, there will remain a finite probability of a mismatch, particularly for nucleotides more removed from the ligation site. The error rate depends on at least two mismatch properties: base pairing (that is, A with G) and distance from the ligation site.

As an illustration of the process to determine the confidence value, consider the two bases in a hexamer probe furthest from the ligation site, numbering the bases as shown here.

where for this particular case the structure is surface-linker-spacer-ATXXXX, focusing on the AT (positions 1 and 2) bases for purpose of the immediate illustration.

To evaluate the possible set of sequences represented, weight matrices are used, following Dayhoff (Dayhoff et al., *A model of evolutionary changes in proteins*, in Atlas of Protein Sequence and Structure, Dayhoff, ed. 1978, National Biomedical Research Foundation: Washington D.C.) and Venezia (Venezia and O'Hara, *Rapid motif compliance scoring with match weight sets*. Comput Appl Biosci, 9(1):65–9 (1993)). The coefficient in these matrices will be determined experimentally for the BEST system. Below is an example of matrices (with illustrative coefficients) representing position 1 and 2, where the columns represent the upper strand nucleotide and the rows represent the lower strand nucleotide. The actual coefficients can be determined empirically.

|   | Position 1 |   |   |   |   | Position 2 |   |   |   |
|---|---|---|---|---|---|---|---|---|---|
|   | A | T | C | G |   | A | T | C | G |
| A | [.02, | .90, | .03, | .05] | A | [.01, | .97, | .01, | .01] |
| T | [.90, | .02, | .03, | .05] | T | [.97, | .01, | .01, | .01] |
| C | [.02, | .03, | .05, | .90] | C | [.01, | .01, | .01, | .97] |
| G | [.03, | .02, | .90, | .05] | G | [.01, | .01, | .97, | .01] |

For the case of a perfect match detection on the hexamer ATXXXX the score is determined to be the product of the coefficients of the matrices, shown below here in bold; 0.90×0.97=0.87.

|   | Position 1 |   |   |   |   | Position 2 |   |   |   |
|---|---|---|---|---|---|---|---|---|---|
|   | A | T | C | G |   | A | T | C | G |
| A | [.02, | .90, | .03, | .05] | A | [.01, | .97, | .01, | .01] |
| T | [.90, | .02, | .03, | .05] | T | [.97, | .01, | .01, | .01] |
| C | [.02, | .03, | .05, | .90] | C | [.01, | .01, | .01, | .97] |
| G | [.03, | .02, | .90, | .05] | G | [.01, | .01, | .97, | .01] |

A case where a singe base mismatch in one strand occurs, for example A→G in position 1 on the hexamer side, the score is determined in a similar fashion, to be 0.05×0.97= 0.05

|   | Position 1 |   |   |   |   | Position 2 |   |   |   |
|---|---|---|---|---|---|---|---|---|---|
|   | A | T | C | G |   | A | T | C | G |
| A | [.02, | .90, | .03, | .05] | A | [.01, | .97, | .01, | .01] |
| T | [.90, | .02, | .03, | .05] | T | [.97, | .01, | .01, | .01] |

```
                        <hexamer>
    surface-spacer-NNNNNNnnnn-ligator-detector-label-3'  <probe>
                        |||||||||||||||||||||||||
    3'-offset-adapter..NNNNNNnnnn-adapter-indexer-5'     <target>
                        123456 <position>

<hexamer>
    surface-linker-spacer-NNNNNNnnnn-ligator-detect-signal-3' <probe>
                          |||||||||||||||||||||||||||
       3'-offset-adapter..NNNNNNNNnnnn-adapter-indexer-5'  <target>
                          123456 <position>
```

-continued

|   | Position 1 | | | | | Position 2 | | | |
|---|---|---|---|---|---|---|---|---|---|
|   | A | T | C | G |   | A | T | C | G |
| C | [.02, | .03, | .05, | .90] | C | [.01, | .01, | .01, | .97] |
| G | [.03, | .02, | .90, | .05] | G | [.01, | .01, | .97, | .01] |

This procedure can be extended to an arbitrary number of bases in a similar manner. For a given number of nucleotides the score can be computed for all possible mismatches and rank ordered to reveal the most probable identity. A cut-off score can be used to reduce the number of possible identities from the matrix estimation. For example using the example matrices above, sequences with a threshold score above 0.50 would yield only one sequence, that being a sequence which matches the probe.

This method of estimating sequences and their respective probability scores from the universe of mismatch events for a said probe can from extended from 1 to n, where n is the number of free bases available for hybridization.

In an organism that has not been completely characterized (i.e. at least sequenced and consensus sequence assembled) a confidence value for uniqueness can be computed if a random distribution of bases is assumed. For example, if there is a candidate of 15 bases in length, in an organism which has an estimated $10^8$ base genome, the 15 base fragment is expected to be unique because $10^8/4^{15}=0.1$ is much less than 1. The genome would have to be 10 times larger before an occurrence of two instances of the particular 15 base fragment would be expected.

The distributions, in known genomes, are known not to be completely random and the initial assumption of a random distribution can be improved as information is gathered. This new information can be used to assign and use confidence values.

As an example, consider a fictitious gene family ABCD, whose members are ABCD1, ABCD2 and ABCD3. The three members were discovered following some event such as heat shock, and they are thus putatively assigned to belong to the heat shock family of genes and happen to have significant stretches of conserved sequence among the family of genes. Also consider the organism to be a plant, where ABCD1 was isolated from the plant root, ABCD2 was isolated from the plant leaf, and ABCD3 was isolated from the plant flower. The estimation matrix may look like

|   | 1 2 3 |
|---|---|
| ABCD1 | [.60, .15, .05] |
| ABCD2 | [.25, .60, .15] |
| ABCD3 | [.05, .15, .60] | where the column 1 represents root, column 2 represents leaf and column 3 represents flower.

In a single experiment where there is a high confidence in the sequence but the sequence may belong to one of the three known members of the family, the source of the sample (i.e. root, leaf or flower) allow estimation of the identity of the gene. For the fully mathematically closed treatment the matrix must contain all elements of the family, here to allow for a still to be found gene in this family, the rows and columns do not add to 1; all the other members are assigned a sum of 0.05, the values to be updated as the amount of information known about the organism increases.

One can extend this estimation to include organism homology. That is, a search of a database of all organisms for a binary sequence tag from gene ABCD1 of Plant 1 may turn up matches to Plant 2, Plant 3, Mammal 1, etc. The estimation matrix would be constructed from the known organism data in the database.

The calculations and analysis described above can be illustrated using the following example of construction of a catalog. Consider a two probe detector array, a control sample, and a tester sample. Consider the two probes to have the known sequences: A. <substrate-linker-AGGGAG-3'>, and, B, <substrate-linker-ATGGAG>. These probes will capture their cognate sequence: AA, < ... TCCCTC ... >, and, BB, < ... TACCTC ... > from the control and tester samples, as well as some mismatched species with lower probability as described herein. Utilizing the estimation matrix technique as discussed above the probabilities of the correct matching can be calculated.

The BEST procedure is conducted on the control and tester, resulting signals are collected from the probe detector array, and a catalog is made which contains the four signals:

|   | control | | | tester | |
|---|---|---|---|---|---|
|   | AA | BB |   | AA | BB |
| A | .30 | .03 | A | .80 | .10 |
| B | .03 | .50 | B | .03 | .50 |

The catalog also contains the probabilities, and/or entries derived from the probabilities, for each probe/target combination, as discussed above. For purpose of illustration let us assume that the probability of having probe sequence A paired with target sequence AA is 0.80, and the probability of having probe sequence A paired with sequence BB is 0.10, probe sequence B paired with target sequence AA is 0.05, and the probability of having probe sequence B paired with sequence BB is 0.75, or

|   | estimation | |
|---|---|---|
|   | AA | BB |
| A | .80 | .10 |
| B | .05 | .75 |

It is a simple matter of application of linear algebra to determine the signals corresponding to each target. Here, for example, multiplying the corresponding entries together to convert the control and tester to the pattern corresponding to the probabilistic pattern of the target of interest. For example, the total signal ascribed, in the control sample, to AA target is 0.30×0.80 (on A probe site, perfect match)+ 0.03×0.05 (on B probe site, imperfect match)= approximately 0.24. On the tester sample, the AA target signal is 0.80×0.80+0.03×0.05=approximately 0.64. Comparison of the pattern for the control and tester, for the sequence corresponding to AA, exhibits an increase in the relative amount of AA from 0.24 to 0.64 for control to tester respectively. All other entries in the pattern are calculated in the same fashion.

Illustrations

The disclosed method can be further understood by way of the following illustrations which involve examples of the disclosed method. The illustrations are not intended to limit the scope of the method in any way.

Illustration 1: Mass Spectrometry Detection.

This illustration is an example of the disclosed method using known enzymes and mass spectrometry for detection. The signals of the control and tester samples are distinguished in the mass spectrometer in that the labeling moieties have different masses. The ratio of the appropriate peaks represents the ratio of the control and tester materials. For the control and tester samples, steps 1–8 are conducted in parallel, with the labels of step 8 being a heavy and a light mass tag for control and tester, respectively. The resulting mixtures for the control and tester are pooled and then contacted, simultaneously, with the array of step 9.

1. Make double stranded cDNA using reverse transcriptase following standard procedures.

2. Digest with restriction endonuclease, MboI which has a ^GATC_ recognition site. Depicted cDNA is SEQ ID NO:9.

```
5'-NNNNNNNNNNGATCNNNNNNNNNNN-3'
   ||||||||||||||||||||||||    + MboI
3'-NNNNNNNNNNCTAGNNNNNNNNNNN-5'
```

↓

```
         (A)                    (B)
5'-NNNNNNNNNN-3'         5'-GATCNNNNNNNNNN-3'
   ||||||||||                  ||||||||||
3'-NNNNNNNNNNCTAG-5'     3'-      NNNNNNNNNN-5'
```

3. Attach offset adapters. These offset adapters contain a Type IIS endonuclease recognition site. The offset adapters are hybridized and ligated to the correct fragments. The example Type IIS enzyme used here is FokI which has recognition and cut positions of GGATG (9/13).

```
    5'-NNNNNNNNNN-3'        5'-GATCATCC..off-adap-3'
(A)    ||||||||||              ||||||||||||||
    3'-NNNNNNNNNNCTAG-5'    3'-TAGG..off-adap-5'

5'-off-adap..GGAT-3'    5'-GATCNNNNNNNNNN-3'
(B)    ||||||||||||||    +     ||||||||||
    3'-off-adap..CCTACTAG-5'    3'-NNNNNNNNNN-5'
```

4. Second digest. Cut with Type IIS restriction endonuclease. For clarity, only the 'B' fragment (GGATGATCNNNNNNNNN; SEQ ID NO:10) is followed below.

```
    5'-off-adap..GGATGATCNNNNNNNNNN-3'
(B)    ||||||||||||||||||||||||||||    + FokI
    3'-off-adap..CCTACTAGNNNNNNNNNN-5'   (GGATG)
```

↓

```
    5'-off-adap..GGATGATCNNNNNN-3'
(B)    |||||||||||||||||||||||
    3'-off-adap..CCTACTAGNNNNNNnnnn-5'
```

5. Divide resulting digest into 256 wells on a 384 microtiter plate. Add adapter-indexer containing a capture tag (biotin in this case), hybridize and ligate to the construct.

```
    5'-off-adap..GGATGATCNNNNNN-3'   5'-nnnn-adapter-indexer-3'
(B)    ||||||||||||||||||||||||||  +    ||||||||||||||
    3'-off-adap..CCTACTAGNNNNNNnnnn-5'    adapter-indexer-Biotin
```

↓

```
    5'-off-adap..GGATGATCNNNNNNnnnn-adapter-indexer-3'
(B)    ||||||||||||||||||||||||||||||||||||||||||||||
    3'-off-adap..CCTACTAGNNNNNNnnnn-adapter-indexer-Biotin
```

5a. Cleanup using biotin-advidin interaction to retain only ligated constructs.

6. Amplify. Two amplification primers are used, one designed to be complementary to a strand of the offset adapter, and another designed to be complementary to the adapter-indexer. A number of phosphorothioate linkages are included in the 3' end of the lower strand; these are used to protect against the exonuclease digest which follows.

Amplicons generated from PCR:

```
    5'-off-adap..GGATGATCNNNNNNnnnn-adapter-indexer-3'
(B)    ||||||||||||||||||||||||||||||||||||||||||||||
    3'-off-adap..CCTACTAGNNNNNNnnnn-adapter-indexer-5'
```

7. Exonuclease digestion step to produce single stranded amplicon.

```
3'-off-adap..CCTACTAGNNNNNNnnnn-adapter-indexer-5'
```

8. Add ligator-detector with a mass label, using different labels for tester and control.

```
                           5'-nnnn-ligator-detect-
                              |||||||||||||||||||| label
3'-off-adap..CCTACTAGNNNNNNnnnn-adapter-indexer-5'
```

9. Localize in array. An array may be constructed which contains up to, in this illustration, all 4096 hexamers. For this illustration consider the array to be on a glass slide, and to contain all 4096 hexamers covalently attached to the slide through a PEG linker-spacer.

Combine the control and tester solutions, and contact the mixture with the array under hybridization conditions. Once hybridized, ligate.

```
                             hexamer
surface----linker-spacer------NNNNNN-3' +

5'-nnnn-ligator-detect-label
                         |||||||||||||||||
           3'-off-adap..CCTACTAGNNNNNNnnnn-adapter-indexer-5'
                                  ↓
*surface--linker-spacer-  ---NNNNNNnnnn-ligator-detect-label
                             ||||||||||||||||||||||||||
           3'-adapter..CCTACTAGNNNNNNnnnn-adapter-indexer-5'
```

10. Detection by MALDI-TOF-MS.

Coat the glass slide with an appropriate matrix material, such as 2,5-dihydroxy benzoic acid or others as known in the art. Place the glass slide in the source region of a MALDI-TOF-MS. Individual hexamer regions are sampled by the laser, which will release the fragments complementary to the strands tethered to the surface, and detected in the time-of-fight spectrometer. Because the control and tester will have different masses in the spectrum, the ratio of the heavy to light mass signals will represent the ratio of control and tester DNA inputs. Notice that this detection method will discriminate against array mismatched samples because a single base mismatch will cause the parent peak to shift by the mass of the base change; such mass accuracy for short oligonucleotides is known in the art.

11. Statistics and error detection.

Recognizing that each restriction cut of step 2 results in two tags, data from correlated tags, in the case of known genomes, are further utilized to error detect and intensity correct. Other options for mass spectroscopy detection are described below.

Illustration 2: Fluorescence Detection on Probe Arrays.

This illustration is an example of the disclosed method using known enzymes, probe arrays on glass slides, and fluorescence readout. The signals of the control and tester samples are distinguished by use of differing fluorescence labels, where the ratio of the appropriate peaks represents the ratio of the control and tester materials. For the control and tester samples, steps 1–8 are conducted in parallel, with the labels of step 8 being a two differing fluorescence tags for control and tester. The mixtures for the control and tester are pooled and then contacted, simultaneously, with the array of step 9.

1. Make double stranded cDNA using reverse transcriptase following standard procedures.

2. Digest with restriction endonuclease, MboI which has a ^GATC_ recognition site. Depicted cDNA is SEQ ID NO:9.

```
     5'-NNNNNNNNNNNGATCNNNNNNNNNNN-3'
        |||||||||||||||||||||||||||    + MboI
     3'-NNNNNNNNNNNCTAGNNNNNNNNNNN-5'

↓

(A)                        (B)
     5'-NNNNNNNNNNN-3'           5'-GATCNNNNNNNNNNN-3'
        |||||||||||                  |||||||||||
     3'-NNNNNNNNNNNCTAG-5'        3'-    NNNNNNNNNNN-5'
```

3. Attach offset adapters. These offset adapters contain a Type IIS endonuclease recognition site. The offset adapters are hybridized and ligated to the correct fragments. The example Type IIS enzyme used here is FokI which has recognition and cut positions of GGATG (9/13).

```
        5'-NNNNNNNNNNN-3'              5'-GATCATCC..off-adap-3'
    (A) |||||||||||                       ||||||||||||
        3'-NNNNNNNNNNNCTAG-5'           3'-TAGG..off-adap-5'

5'-off-adap..CGAT-3'            5'-GATCNNNNNNNNNNN-3'
    (B) ||||||||||||||       +            |||||||||||
        3'-off-adap..CCTACTAG-5'        3'-NNNNNNNNNNN-5'
```

4. Second digest. Cut with Type IIS restriction endonuclease. For clarity, only the 'B' fragment (GGATGATCNNNNNNNNNN; SEQ ID NO:10) is followed below.

```
        5'-off-adap..GGATGATCNNNNNNNNNNN-3'
    (B) ||||||||||||||||||||||||||||||    + FokI
        3'-off-adap..CCTACTAGNNNNNNNNNNN-5'   (GGATG)

↓

5'-off-adap..GGATGATCNNNNN-3'
    (B) ||||||||||||||||||||||||
        3'-off-adap..CCTACTAGNNNNNnnnn-5'
```

5. Divide resulting digest into 256 wells on a 384 microtiter plate. Add adapter-indexer containing a capture moiety (biotin in this case), hybridize and ligate to the construct.

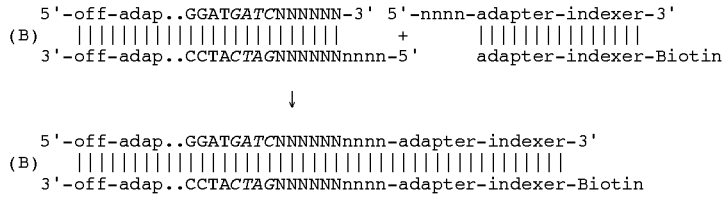

5a. Cleanup using biotin-advidin interaction to retain only ligated constructs.

6. Amplify. Two amplification primers are used, one designed to be complementary to a strand of the offset adapter, and another designed to be complementary to the adapter-indexer. A number of phosphorothioate linkages are included in the 3' end of the lower strand; these are useful to protect against the exonuclease digest which follows.

Amplicons generated from PCR:

7. Exonuclease digestion step to produce single stranded amplicon.

```
3'-off-adap..CCTACTAGNNNNNNnnnn-adapter-indexer-5'
```

8. Add ligator-detector.

9. Localize in array. An array may be constructed which contains, for example, up to all 4096 hexamers. For this illustration consider the array to be on a glass slide, and to contain all 4096 hexamers covalently attached to the slide through a PEG linker-spacer.

Combine the control and tester solutions, and contact the mixture with the array under hybridization conditions. Once hybridized, ligate.

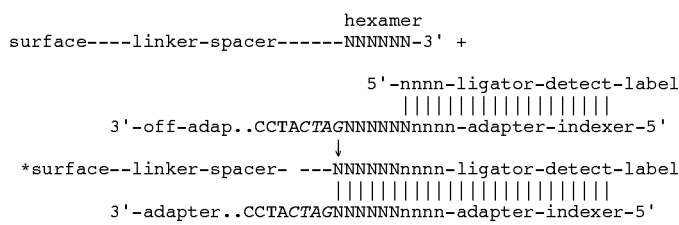

10. Detection by fluorescence.

Place the glass slide into a slide scanner capable of at least two color detection (several such instruments are commercially available, for example products from GSI Lumonics, Axon, Virtek, and others). Because the control and tester will have different colors, the ratio of the signals in the two colors will represent the ratio of control and tester DNA inputs. Other options for label detection are described below.

Illustration 3: Labels and Sorting.

The following illustration makes use of labels, sorting, and microbeads in the disclosed method. In this illustration, 256 types of ligator-detector are each coupled to the surface of 256 different color encoded microbeads, thus each ligator-detector is identified by a single color. After annealing and ligating these new "microbead ligator-detectors" to the target sequences, the 256 sets of microbead ligator-detectors are loaded simultaneously in a 4096-well microtiter plate containing 4096 hexamer probes, one probe per well. Only a perfect match during hybridization will ligate a fluorochrome-labeled hexamer to a specific microbead labeled complex. The Luminex100 (Luminex Corporation) flow analyzer can distinguish color encoded microbeads and measure their fluorescence simultaneously, the six bases adjacent to the ligator-detector can be identified by knowing the specific address (and the hexamer contained at that address) of the wells on the microtiter plate. The design is illustrated below.

The steps up to generation of the single-stranded amplicon are the same as basic BEST, including enzyme cuts, offset adaptor ligation, Type IIS enzyme cuts, adaptor-indexer ligation, PCR amplification, and capturing and denaturing the fragments to generate single-strands of binary sequence tags.

The 256 single stranded binary sequence tags are annealed to 256 ligator-detectors. There are 256 different sequences of ligator-detectors, which comprise the 256 different ligator-detectors complementary to each of the 4-base sticky ends generated. The ligator-detector is labeled with a signaling moiety, such as a fluorescent dye or a fluorescent bead. Each of the 256 annealed single stranded preparations is split into 4096 aliquots and hybridized to one of 4096 hexamer probes. For example, the 4096 hexamers are contained in a 4096 well microtiter plate, with each well containing a single hexamer probe. Each of the 4096 hexamer probes is fluorescently labeled at the 5'-end and contains a free 3'-hydroxyl end.

Following hybridization and ligation of the hexamer probe with the annealed single-stranded amplicons, the 256 preparations are transferred to another well containing streptavidin and unbound material is washed away (the hexamer probe also contains a biotin group). Two signals are then measured.

One signal corresponds to the sample (either tester or control, for instance). Tester and control samples are distinguished by fluorescently encoded beads (Luminex). In one embodiment, 512 colors can be used; 256 colors for the tester and 256 colors for the control. However, 256 color encoded beads could also be used where the beads are "offset" between the tester and control. For instance, color 1 corresponds to hexamer 2 for the tester but hexamer 3 for the control, and so on. The second signal derives from the labeled hexamer probe and measures the level of the single-stranded DNA annealed to the ligator-detector. The two signals measured here could be read simultaneously on an instrument such as the Luminex 100.

Illustration 4: BEST with Early Amplification.

In some cases, particularly for the detection of very low abundance mRNA, an early amplification is beneficial. In illustrations 1 and 2 above, the sample is divided into 256 aliquots prior to an amplification step. In an initial sample with a plurality of cDNA molecules, some species are expected to be present at concentrations below the detectable limit of the system after being divided into the 256 aliquots. To overcome such a concentration limitation, the following form of the method introduces an amplification step prior to dividing the sample into 256 equivalent pools.

1. Make double stranded cDNA.

2. Select a set of restriction enzymes that includes both Type IIS and Type II restriction enzymes. The sets can be designed to address different experimental outcomes through the selection of recognition sites, number of bases in the recognition site, reach of the Type IIS enzyme, etc., with the design such that all or most of the unknown bases between the two restriction sites are determined. Here FokI (IIS) and MboI (II) are utilized.

3. First digest cDNA with Type II restriction endonuclease, 4 base overhang on the 5' end is preferred. MboI has the recognition site ^GATC. Depicted cDNA is SEQ ID NO:9.

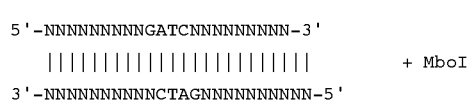

yields two fragments. (A) and (B)

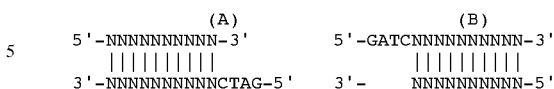

4. Add an offset adapter that contains a Type IIS recognition site by hybridization and ligation. Here the Type IIS is FokI with the recognition site GGATG(9/13). This adapter also contains a region to be used as a universal primer for a PCR in a later step, call the region UP1.

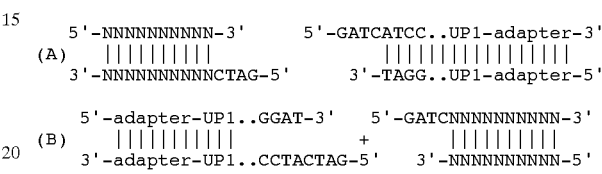

5. Second digest. Type IIS restriction endonuclease. The nascent constructs are digested using FokI. For clarity, only the 'B' fragment (GGATGATCNNNNNNNNNN; SEQ ID NO:10) is followed below.

yields

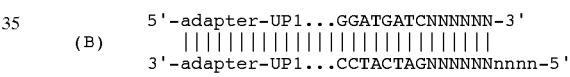

6. Add a plurality of adapter-indexers. There are 256 different types of adapter-indexers, each adapter is constructed with a common section encoding a universal primer (UP2) an adapter-specific PCR section (AS1) followed by a adapter-specific 4 base 5' overhang. A possible AS1 would be the complement of the 4 base 5'-overhang.

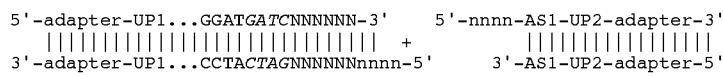

To yield

7. PCR amplify using universal primers complementary to UP1 and UP2. This round of amplifications would yield amplification on the order of 500 times.

8. Divide amplicons into plurality of wells. Here consider all 256 possibilities and transfer to 256 wells of a 384 well microtiter plate.

9. Perform further PCR. Now use universal primers for UP1 with biotin attached and the second primer is specific for a particular AS1, thus specific (1 of 256) biotinylated adapter specific amplicons are generated.

```
     biotin-5'-adapter-UP1...GGATGATCNNNNNNnnnn-AS1-UP2-adapter-3'
(B)                |||||||||||||||||||||||||||||||||||||||||||||||
              3'-adapter-UP1...CCTACTAGNNNNNNnnnn-AS1-UP2-adapter-5'
```

10. The remaining steps mirror those disclosed in Illustration 1.

Cleanup using biotin-advidin interaction to retain constructs, create single stranded fragments:

```
3'-adapter-UP1...CCTACTAGNNNNNNnnnn-AS1-UP2-
adapter-5'
```

Add ligator-detector:

```
                    5'-nnnn-AS1-UP2-ligator-detect-signal
                       |||||||||||||||||||||||||||||||||
3'-adapter-UP1...CCTACTAGNNNNNNnnnn-AS1-UP2-adapter-indexer-5'
```

Hybridize to probe array of 4096 hexamers:

```
surface-linker-spacer--NNNNNNnnnn-AS1-UP2-ligator-detect-signal
                       |||||||||||||||||||||||||||||||||||||||
     3'-adapter..CCTACTAGNNNNNNnnnn-AS1-UP2-adapter-indexer-5'
```

Detect by mass spectrometry (or fluorescence, if the label is fluorometric as in Illustration 2).

Illustration 5: Pyrosequencing.

Detection of binary sequence tags may be made by any sequencing technique known in the art. A preferred technique is pyrosequencing. A preferred instrument for this is available from Pyrosequencing AB, Vallongatan 1, SE-752 28 Uppsala, Sweden. Using this instrument the unknown bases between the Type II and Type IIS recognition sites may be sequenced in the following manner.

1. Make double stranded cDNA
2. Cleave with Type II enzyme, preferably one with a 4 base recognition and 4 base 5' overhang.
3. Prepare offset adapters having the Type IIS recognition site and the compatible overhang to the overhang of the Type II cleavage in the manner described in illustration 1.
4. Hybridize and ligate the offset adapter to the cleaved fragments from step 2.
5. Cleave the cDNA with Type IIS enzyme which cleaves at a site offset from the recognition sequence introduced by the addition of offset adaptors.
6. Distribute the solution from step 5 into 256 replicate instances in 256 wells of a 384 well microtiter plate. These are index samples.
7. Ligate indexing adapters. Each index sample is incubated with a different adapter-indexer each of which has a sticky end compatible with one of the possible sticky ends on the DNA fragments in that index sample. The adapter-indexers are then coupled onto compatible DNA fragments by ligation, resulting in the formation of binary sequence tags with adapters covalently attached to each end.
8. Dilute. Each index sample of binary sequence tags is diluted to achieve a concentration of less than one molecule per well when the sample is distributed to 96, 384, or 1536 well microtiter plates in the following step. The dilution will depend upon a number of factors including the number of wells into which the sample subsequently is distributed, the Type II cleavage frequency, and the initial input amount of DNA.

9. Distribute. The contents of each of the wells of step 8, which contain one type of adapter indexer each, are distributed to a number of wells. In this illustration, each well is transferred to 96 wells, for a total of 256 microtiter plates.

10. Amplify. Each aliquot of the binary sequence tags is amplified using a suitable amplification method, such as PCR. Two PCR primers are used, one designed to be complementary to a sequence of the offset-adapter and the other designed to be complementary to the adapter-indexer. Because there should only be one molecule in the well which can be amplified, there should be one predominant molecular species following the amplification.

11. Cleanup. The amplified binary sequence tags may be cleaned up using any number of methods known in the art. The preferred method is to have a capture tag incorporated in the PCR primer, for example biotin, such that single stranded amplicons are retained for further steps.

12. Detection by Pyrosequencing. Using a sequencing primer complementary to one of the adapter sequences the unknown, adjacent bases can be directly determined through the technique of pyrosequencing. Because there is predominantly one single stranded DNA fragment from each well, there should be one predominant sequence corresponding to that fragment. The commercial instrument is capable of sequencing ten bases per well, for 96 wells, in about 10 minutes. The expression level of a given binary sequence tag is proportional to the number of times the sequence occurs.

Illustration 6: Hairpin Primers.

This illustration describes the use of hairpin primers. The method described in illustration 1 can be adapted to make use of a cleavable hairpin primer and release the tag in the following fashion:

1. Produce binary sequence tags as in Illustration 1 and then perform the PCR step using a hairpin primer, the hairpin primer containing a uracil in the hairpin sequence, or near the hairpin sequence. The hairpin primer is a nucleic acid molecule that contains a primer sequence and that can form a stem-loop or hairpin structure. A hairpin structure forms at the end of the amplified fragments and facilitates coupling of the fragments to the probes (see next step). The hairpin structure serves the function of the ligator-detector hybridized to a binary sequence tag by forming a duplex region next to a single-stranded region. This allows the end of the amplified fragment to be ligated to a probe array (see next step).

2. Hybridize and ligate onto the probe hexamer array.

```
xxxxxxNNNNNNNNNNNNNNN
||||||||||||||||||   U  Labile Hairpin (control)
...nnnnnnnnnnNNNNNNNNNNN xxxxxxNNNNNNNNNNNNNNN
||||||||||||||||||   U  Labile Hairpin (tester)
...nnnnnnnnnnNNNNNNNNNNNM
``` where x is the hexamer probe, N is the hairpin, M is an additional base or bases, n is the binary sequence tag, | indicates base pairing.

3. Wash with alkali to remove non-ligated tag-hairpins.
4. Cleave with uracil-DNA glycosylase.
The released fragment to be analyzed will be:

```
...nnnnnnnnnnNNNNNNNNNNN                (control)

...nnnnnnnnnnNNNNNNNNNNNM               (tester)
```

5. Detect the cleaved tags, resolving, the two different masses, using MALDI-TOF. Use of a tandem mass spectrometer, as described above, to fragment the cleaved tags will determine some or all of the tag sequence, and improve the signal to noise.

Hairpin primers may be utilized to multiplex the readout of the control and tester of a tag from the same address of an surface array.

1. Produce binary sequence tags from cDNA as in Illustration 1 and then generate PCR products using hairpin primers. Use different hairpin primers for the tester and control, a uracil in the synthetic adapters for the testers and a thymine in the synthetic adapters for the controls. A fluorescence label my be incorporated into the hairpin using standard fluorescent labeled nucleotides.

2. Hybridize and ligate to probe array.

```
xxxxxxNNNNNNNNNNNNNNN
||||||||||||||||||   dT  (Stable Hairpin, Control)
...nnnnnnnnnnNNNNNNNNN*NN xxxxxxNNNNNNNNNNNNNNN
||||||||||||||||||   U   (Labile Hairpin, Tester)
...nnnnnnnnnnNNNNNNNNN*NN
``` where x is the hexamer probe, N is the hairpin, n is the binary sequence tag, | indicates base pairing, * indicates a fluorescently labeled nucleotide.

3. Read signal before uracil-DNA glycosylase, this corresponds to control plus tester total signal.

4. Cleave hairpins containing uracil using uracil-DNA glycosylase. The thymine containing hairpin will remain intact.

5. Wash the slide.

6. Read signal AFTER uracil-DNA glycosylase, this corresponds to control signal only.

Illustration 7: MAABST with Mass Spectrometry Detection.

This illustration is a detailed look using known enzymes and mass spectrometry for detection. The signals of the control and tester samples are distinguished in the mass spectrometer in that the signalings moieties have different masses, where the ratio of the appropriate peaks represents the ratio of the control and tester materials.

1. Make double stranded cDNA.

2. Digest with a methylation sensitive restriction endonuclease. Depicted cDNA is SEQ ID NO:9.

```
                        CH3
                         |
5'-NNNNNNNNNNNGATCNNNNNNNNNNN-3'
   |||||||||||||||||||||||||||   + methyl sensitive RE
3'-NNNNNNNNNNNCTAGNNNNNNNNNNN-5'
                         ↓
                        CH3
                         |
5'-NNNNNNNNNNNGATCNNNNNNNNNNN-3'
   |||||||||||||||||||||||||||   if nucleic acid is methylated
3'-NNNNNNNNNNNCTAGNNNNNNNNNNN-5'

(A)                         (B)
5'-NNNNNNNNNNN-3'           5'-GATCNNNNNNNNNNN-3'
   |||||||||||                  |||||||||||
3'-NNNNNNNNNNNCTAG-5'       3'-     NNNNNNNNNNN-5'
``` if nucleic acid is unmethylated

3 Create Type IIS constructs. Add offset adapter encoding a Type IIS endonuclease by hybridization and ligation. FokI=GGATG(9/13).

```
                        CH3
                         |
5'-NNNNNNNNNNNGATCNNNNNNNNNNN-3'
   |||||||||||||||||||||||||||
3'-NNNNNNNNNNNCTAGNNNNNNNNNNN-5'
```
if nucleic acid is methylated, sequence is not cut and ligation is not possible, and no binary sequence tags are generated if DNA is cut, offset adapter is ligated:

```
      5'-NNNNNNNNNNN-3'         5'-GATCATCC..adapter-3'
(A)      |||||||||||                |||||||||||||
      3'-NNNNNNNNNNNCTAG-5'     3'-TAGG..adapter-5'

5'-off-adap..GGAT-3'      5'-GATCNNNNNNNNNNN-3'
(B)      |||||||||||||    +        |||||||||||
      3'-off-adap..CCTACTAG-5'  3'-NNNNNNNNNNN-5'
```

4. Second digest, Type IIS restriction endonuclease. For clarity, only the 'B' fragment (GGATGATCNNNNNNNNNN; SEQ ID NO:10) is followed below.

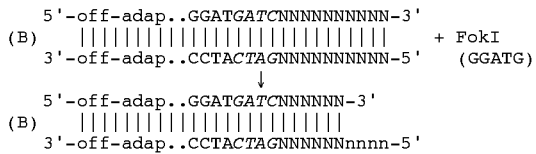

5. Divide cDNA digest into 256 wells on a 384 microtiter plate. Add immobilizing indexer adapter and ligate to construct.

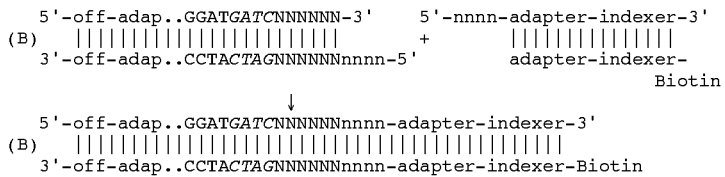

5a. Cleanup using biotin-advidin interaction to retain constructs.

6. Amplification. Two amplification primers are used, one designed to be complementary to a strand of the offset adapter, and another designed to be complementary to the adapter-indexer. A number of phosphorothioate linkages are included in the 3' end of the lower strand; these are necessary to protect against the exonuclease digest which follows.

Amplicons generated from PCR

7. Exonuclease digestion step to produce single stranded amplicon.

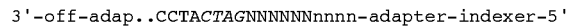

8. Add ligator-detector.

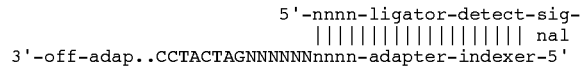

9. Hybridize to solid surface index of 4096 hexamers. Ligate.

10. Place the surface in the source region of a MALDI-TOF-MS. Individual hexamer regions are sampled by the laser and detected in the time-of-fight spectrometer. Ratio of the heavy to light mass signals will represent the ratio of control and tester DNA inputs. As an option, the mass of the DNA strand itself and/or it's fragmentation pattern can be used to verify that the hexamer was correctly hybridized and will provide additional control/tester ratio information.

11. Recognizing that each restriction cut of step 2 results in two tags, data from correlated binary sequence tags, in the case of known genomes, are further utilized to error detect and correct.

It is understood that the disclosed invention is not limited to the particular methodology, protocols, and reagents described as these may vary. It is also to be understood that the terminology used herein is for the purpose of describing particular embodiments only, and is not intended to limit the scope of the present invention which will be limited only by the appended claims.

It must be noted that as used herein and in the appended claims, the singular forms "a", "an", and "the" include plural reference unless the context clearly dictates otherwise. Thus, for example, reference to "a host cell" includes a plurality of such host cells, reference to "the antibody" is a reference to one or more antibodies and equivalents thereof known to those skilled in the art, and so forth.

Unless defined otherwise, all technical and scientific terms used herein have the same meanings as commonly understood by one of skill in the art to which the disclosed invention belongs. Although any methods and materials similar or equivalent to those described herein can be used in the practice or testing of the present invention, the preferred methods, devices, and materials are as described. Publications cited herein and the material for which they are cited are specifically incorporated by reference. Nothing herein is to be construed as an admission that the invention is not entitled to antedate such disclosure by virtue of prior invention.

Those skilled in the art will recognize, or be able to ascertain using no more than routine experimentation, many equivalents to the specific embodiments of the invention described herein. Such equivalents are intended to be encompassed by the following claims.

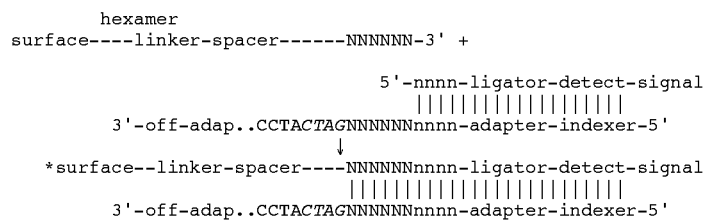

We claim:

1. A method of producing binary sequence tags from nucleic acid fragments in a nucleic acid sample, the method comprising (a) incubating a nucleic acid sample with one or more first nucleic acid cleaving reagents to produce nucleic acid fragments, wherein the first nucleic acid cleaving reagents are not type IIS restriction enzymes, (b) mixing one or more offset adaptors with the nucleic acid sample and covalently coupling the offset adaptors to the nucleic acid fragments, (c) incubating the nucleic acid sample with one or more second nucleic acid cleaving reagents to produce nucleic acid fragments with sticky ends, wherein the second nucleic acid cleaving reagents cleave at a site offset from their recognition sequence, wherein each offset adaptor has a recognition sequence for at least one of the second nucleic acid cleaving reagents, (d) mixing one or more adaptor-indexers with the nucleic acid sample and covalently coupling the adaptor-indexers to the nucleic acid fragments, wherein each adaptor-indexer has a different sticky end, wherein each sticky end of the adaptor-indexers is compatible with one of the possible sticky ends that could be generated by the second nucleic acid cleaving reagents, wherein the nucleic acid fragments to which offset adaptors and adaptor-indexers have been coupled are binary sequence tags.

2. A method of producing binary sequence tags from nucleic acid fragments in a nucleic acid sample, the method comprising (a) incubating a nucleic acid sample with one or more first nucleic acid cleaving reagents to produce nucleic acid fragments, wherein the first nucleic acid cleaving reagents are not type IIS restriction enzymes, (b) mixing one or more first offset adaptor strands with the nucleic acid sample and covalently coupling the first offset adaptor strands to the nucleic acid fragments, wherein, after coupling, the first offset adaptor strands are fully or partially single-stranded, (c) treating the nucleic acid sample to result in full or partial complementary sequences hybridized to the first offset adaptor strands, (d) incubating the nucleic acid sample with one or more second nucleic acid cleaving reagents to produce nucleic acid fragments with sticky ends, wherein the second nucleic acid cleaving reagents cleave at a site offset from their recognition sequence, wherein each first offset adaptor strand has a recognition sequence for at least one of the second nucleic acid cleaving reagents, (e) mixing one or more adaptor-indexers with the nucleic acid sample and covalently coupling the adaptor-indexers to the nucleic acid fragments, wherein each adaptor-indexer has a different sticky end, wherein each sticky end of the adaptor-indexers is compatible with one of the possible sticky ends that could be generated by the second nucleic acid cleaving reagents, wherein the nucleic acid fragments to which first offset adaptor strands and adaptor-indexers have been coupled are binary sequence tags.

3. A method of producing binary sequence tags from nucleic acid fragments in a nucleic acid sample, the method comprising (a) incubating a nucleic acid sample with one or more first nucleic acid cleaving reagents to produce nucleic acid fragments, wherein the first nucleic acid cleaving reagents are not type IIS restriction enzymes, (b) mixing one or more offset adaptors with the nucleic acid sample and covalently coupling the offset adaptors to the nucleic acid fragments, (d) incubating the nucleic acid sample with one or more second nucleic acid cleaving reagents to produce nucleic acid fragments with sticky ends, wherein the second nucleic acid cleaving reagents cleave at a site offset from their recognition sequence, wherein each offset adaptor has a recognition sequence for at least one of the second nucleic acid cleaving reagents, (e) mixing one or more first adaptor-indexer strands with the nucleic acid sample and covalently coupling the first adaptor-indexer strands to the nucleic acid fragments, wherein each first adaptor-indexer strand has a different end sequence, wherein each end sequence of the first adaptor-indexer strands is compatible with one of the possible sticky ends that could be generated by the second nucleic acid cleaving reagents, wherein, after coupling, the first adaptor-indexer strands are fully or partially single-stranded, wherein the nucleic acid fragments to which offset adaptors and first adaptor-indexer strands have been coupled are binary sequence tags.

4. A method of producing binary sequence tags from nucleic acid fragments in a nucleic acid sample, the method comprising (a) incubating a nucleic acid sample with one or more first nucleic acid cleaving reagents to produce nucleic acid fragments, wherein the first nucleic acid cleaving reagents are not type IIS restriction enzymes, (b) mixing one or more first offset adaptor strands with the nucleic acid sample and covalently coupling the first offset adaptor strands to the nucleic acid fragments, wherein, after coupling, the first offset adaptor strands are fully or partially single-stranded, (c) treating the nucleic acid sample to result in full or partial complementary sequences hybridized to the first offset adaptor strands, (d) incubating the nucleic acid sample with one or more second nucleic acid cleaving reagents to produce nucleic acid fragments with sticky ends, wherein the second nucleic acid cleaving reagents cleave at a site offset from their recognition sequence, wherein each first offset adaptor strand has a recognition sequence for at least one of the second nucleic acid cleaving reagents, (e) mixing one or more first adaptor-indexer strands with the nucleic acid sample and covalently coupling the first adaptor-indexer strands to the nucleic acid fragments, wherein each first adaptor-indexer strand has a different end sequence, wherein each end sequence of the first adaptor-indexer strands is compatible with one of the possible sticky ends that could be generated by the second nucleic acid cleaving reagents, wherein, after coupling, the first adaptor-indexer strands are fully or partially single-stranded, wherein the nucleic acid fragments to which first offset adaptor strands and first adaptor-indexer strands have been coupled are binary sequence tags.

5. A method of producing binary sequence tags from nucleic acid fragments in a nucleic acid sample, the method comprising covalently coupling one or more offset adaptors to nucleic acid fragments with sticky ends produced by digestion of a nucleic acid sample with one or more first nucleic acid cleaving reagents, wherein the first nucleic acid cleaving reagents are not type IIS restriction enzymes, covalently coupling one or more adaptor-indexers to the nucleic acid fragments, wherein the nucleic acid fragments have sticky ends produced by digestion with one or more second nucleic acid cleaving reagents, wherein the second nucleic acid cleaving reagents cleave at a site offset from their recognition sequence, wherein each offset adaptor has a recognition sequence for at least one of the second nucleic acid cleaving reagents, wherein each adaptor-indexer has a different sticky end, wherein each sticky end of the adaptor-indexers is compatible with one of the possible sticky ends that could be generated by the second nucleic acid cleaving reagents, wherein the nucleic acid fragments to which offset adaptors and adaptor-indexers have been coupled are binary sequence tags.

6. The method of claim 5 wherein the first nucleic acid cleaving reagents do not cleave at a site offset from their recognition sequence.

7. The method of claim 5 wherein the first nucleic acid cleaving reagents cleave within the recognition sequence.

8. The method of claim 5 wherein at least one of the first nucleic acid cleaving reagents is a Type II restriction enzyme.

9. A method of producing binary sequence tags from nucleic acid fragments in a nucleic acid sample, the method comprising covalently coupling one or more first offset adaptor strands to nucleic acid fragments with sticky ends produced by digestion of a nucleic acid sample with one or more first nucleic acid cleaving reagents, wherein, after coupling, the first offset adaptor strands are fully or partially single-stranded, wherein the first nucleic acid cleaving reagents are not type IIS restriction enzymes, treating the nucleic acid sample to result in full or partial complementary sequences hybridized to the first offset adaptor strands, covalently coupling one or more adaptor-indexers to the nucleic acid fragments, wherein the nucleic acid fragments have sticky ends produced by digestion with one or more second nucleic acid cleaving reagents, wherein the second nucleic acid cleaving reagents cleave at a site offset from their recognition sequence, wherein each first offset adaptor strand has a recognition sequence for at least one of the second nucleic acid cleaving reagents, wherein each adaptor-indexer has a different sticky end, wherein each sticky end of the adaptor-indexers is compatible with one of the possible sticky ends that could be generated by the second nucleic acid cleaving reagents, wherein the nucleic acid fragments to which first offset adaptor strands and adaptor-indexers have been coupled are binary sequence tags.

10. A method of producing binary sequence tags from nucleic acid fragments in a nucleic acid sample, the method comprising covalently coupling one or more offset adaptors to nucleic acid fragments produced by digestion of a nucleic acid sample with one or more first nucleic acid cleaving reagents, wherein the first nucleic acid cleaving reagents are not type IIS restriction enzymes, covalently coupling one or more first adaptor-indexer strands to the nucleic acid fragments, wherein the nucleic acid fragments have sticky ends produced by digestion with one or more second nucleic acid cleaving reagents, wherein the second nucleic acid cleaving reagents cleave at a site offset from their recognition sequence, wherein each first offset adaptor strand has a recognition sequence for at least one of the second nucleic acid cleaving reagents, wherein each first adaptor-indexer strand has a different end sequence, wherein each end sequence of the first adaptor-indexer strands is compatible with one of the possible sticky ends that could be generated by the second nucleic acid cleaving reagents, wherein, after coupling, the first adaptor-indexer strands are fully or partially single-stranded, wherein the nucleic acid fragments to which offset adaptors and first adaptor-indexer strands have been coupled are binary sequence tags.

11. A method of producing binary sequence tags from nucleic acid fragments in a nucleic acid sample, the method comprising covalently coupling one or more first offset adaptor strands to nucleic acid fragments with sticky ends produced by digestion of a nucleic acid sample with one or more first nucleic acid cleaving reagents, wherein, after coupling, the first offset adaptor strands are fully or partially single-stranded, wherein the first nucleic acid cleaving reagents are not type IIS restriction enzymes, treating the nucleic acid sample to result in full or partial complementary sequences hybridized to the first offset adaptor strands, covalently coupling one or more first adaptor-indexer strands to the nucleic acid fragments, wherein the nucleic acid fragments have sticky ends produced by digestion with one or more second nucleic acid cleaving reagents, wherein the second nucleic acid cleaving reagents cleave at a site offset from their recognition sequence, wherein each first offset adaptor strand has a recognition sequence for at least one of the second nucleic acid cleaving reagents, wherein each first adaptor-indexer strand has a different end sequence, wherein each end sequence of the first adaptor-indexer strands is compatible with one of the possible sticky ends that could be generated by the second nucleic acid cleaving reagents, wherein, after coupling, the first adaptor-indexer strands are fully or partially single-stranded, wherein the nucleic acid fragments to which first offset adaptor strands and first adaptor-indexer strands have been coupled are binary sequence tags.

12. A method of producing binary sequence tags from nucleic acid fragments in a nucleic acid sample, the method comprising covalently coupling one or more offset adaptors to nucleic acid fragments produced by digestion of a nucleic acid sample with one or more first nucleic acid cleaving reagents, covalently coupling one or more adaptor-indexers to the nucleic acid fragments, wherein the nucleic acid fragments have sticky ends produced by digestion with one or more second nucleic acid cleaving reagents, wherein the second nucleic acid cleaving reagents cleave at a site offset from their recognition sequence, wherein each offset adaptor has a recognition sequence for at least one of the second nucleic acid cleaving reagents, wherein each adaptor-indexer has a different sticky end, wherein each sticky end of the adaptor-indexers is compatible with one of the possible sticky ends that could be generated by the second nucleic acid cleaving reagents, wherein the nucleic acid fragments to which offset adaptors and adaptor-indexers have been coupled are binary sequence tags, mixing a plurality of ligator-detectors with the binary sequence tags and a detector array comprising one or more probes, and covalently coupling the ligator-detectors to the probes, wherein each ligator-detector comprises sequence matching or complementary to all or part of sequence including, and adjacent to, the sticky end of at least one of the adaptor-indexers, wherein each probe has a different sequence, and detecting, directly or indirectly, coupling of ligator-detectors to the detector array probes.

13. A method of producing binary sequence tags from nucleic acid fragments in a nucleic acid sample, the method comprising covalently coupling one or more offset adaptors to nucleic acid fragments with sticky ends produced by digestion of a nucleic acid sample with one or more first nucleic acid cleaving reagents, wherein the first nucleic acid cleaving reagents are not type IIS restriction enzymes, covalently coupling one or more adaptor-indexers to the nucleic acid fragments, wherein the nucleic acid fragments have sticky ends produced by digestion with one or more second nucleic acid cleaving reagents, wherein the second nucleic acid cleaving reagents cleave at a site offset from their recognition sequence, wherein the second nucleic acid cleaving reagents do not cleave in the recognition sequences of the first nucleic acid cleaving reagents, wherein each offset adaptor has a recognition sequence for at least one of the second nucleic acid cleaving reagents, wherein each adaptor-indexer has a different sticky end, wherein each sticky end of the adaptor-indexers is compatible with one of the possible sticky ends that could be generated by the second nucleic acid cleaving reagents, wherein the nucleic acid fragments to which offset adaptors and adaptor-indexers have been coupled are binary sequence tags.

14. A method of producing binary sequence tags from nucleic acid fragments in a nucleic acid sample, the method comprising (a) incubating a nucleic acid sample with one or more first nucleic acid cleaving reagents to produce nucleic acid fragments, (b) mixing one or more offset adaptors with the nucleic acid sample and covalently coupling the offset adaptors to the nucleic acid fragments, (c) incubating the nucleic acid sample with one or more second nucleic acid cleaving reagents to produce nucleic acid fragments with sticky ends, wherein the second nucleic acid cleaving reagents cleave at a site offset from their recognition sequence, wherein each offset adaptor has a recognition sequence for at least one of the second nucleic acid cleaving reagents, (d) mixing one or more adaptor-indexers with the nucleic acid sample and covalently coupling the adaptor-indexers to the nucleic acid fragments, wherein each adaptor-indexer has a different sticky end, wherein each sticky end of the adaptor-indexers is compatible with one of the possible sticky ends that could be generated by the second nucleic acid cleaving reagents, wherein the nucleic acid fragments to which offset adaptors and adaptor-indexers have been coupled are binary sequence tags, (e) mixing one or more ligator-detectors with the binary sequence tags, wherein each ligator-detector comprises sequence matching or complementary to all or part of sequence including, and adjacent to, the sticky end of at least one of the adaptor-indexers, (f) mixing the nucleic acid sample with a detector array comprising one or more probes and covalently coupling the ligator-detectors to the probes, wherein each probe has a different sequence, and (g) detecting, directly or indirectly, coupling of ligator-detectors to the detector array probes.

15. A method of producing binary sequence tags from nucleic acid fragments in a nucleic acid sample, the method comprising (a) incubating a nucleic acid sample with one or more first nucleic acid cleaving reagents to produce nucleic acid fragments, (b) mixing one or more offset adaptors with the nucleic acid sample and covalently coupling the offset adaptors to the nucleic acid fragments, (c) incubating the nucleic acid sample with one or more second nucleic acid cleaving reagents to produce nucleic acid fragments with sticky ends, wherein the second nucleic acid cleaving reagents cleave at a site offset from their recognition sequence, wherein the second nucleic acid cleaving reagents do not cleave in the recognition sequences of the first nucleic acid cleaving reagents, wherein each offset adaptor has a recognition sequence for at least one of the second nucleic acid cleaving reagents, (d) mixing one or more adaptor-indexers with the nucleic acid sample and covalently coupling the adaptor-indexers to the nucleic acid fragments, wherein each adaptor-indexer has a different sticky end, wherein each sticky end of the adaptor-indexers is compatible with one of the possible sticky ends that could be generated by the second nucleic acid cleaving reagents, wherein the nucleic acid fragments to which offset adaptors and adaptor-indexers have been coupled are binary sequence tags.

* * * * *

SEQUENCE LISTING

<160> NUMBER OF SEQ ID NOS: 10

<210> SEQ ID NO 1
<211> LENGTH: 25
<212> TYPE: DNA
<213> ORGANISM: Artificial Sequence
<220> FEATURE:
<223> OTHER INFORMATION: Description of Artificial Sequence:
      Ligator-detector

<400> SEQUENCE: 1
gcatgcggat cctaaggctt acgcc                                          25

<210> SEQ ID NO 2
<211> LENGTH: 24
<212> TYPE: DNA
<213> ORGANISM: Artificial Sequence
<220> FEATURE:
<223> OTHER INFORMATION: Description of Artificial Sequence:
      Ligator-detector

<400> SEQUENCE: 2
ggcgtaagcc ttaggatccg catc                                           24

<210> SEQ ID NO 3
<211> LENGTH: 24
<212> TYPE: DNA
<213> ORGANISM: Artificial Sequence
<220> FEATURE:
<223> OTHER INFORMATION: Description of Artificial Sequence:
      Ligator-detector

<400> SEQUENCE: 3
caagtaatgg aagctggatt cgcg                                           24

<210> SEQ ID NO 4
<211> LENGTH: 24
<212> TYPE: DNA
<213> ORGANISM: Artificial Sequence
<220> FEATURE:
<223> OTHER INFORMATION: Description of Artificial Sequence:
      Ligator-detector

<400> SEQUENCE: 4
cgcgaatcca gcttccatta cttg                                           24

<210> SEQ ID NO 5
<211> LENGTH: 18
<212> TYPE: DNA
<213> ORGANISM: Artificial Sequence
<220> FEATURE:
<223> OTHER INFORMATION: Description of Artificial Sequence: Primer

<400> SEQUENCE: 5
tttttttttt tttttgc                                                   18

<210> SEQ ID NO 6
<211> LENGTH: 18
<212> TYPE: DNA
<213> ORGANISM: Artificial Sequence
<220> FEATURE:
<223> OTHER INFORMATION: Description of Artificial Sequence: Primer

<400> SEQUENCE: 6
tttttttttt tttttgt                                                   18

```
<210> SEQ ID NO 7
<211> LENGTH: 18
<212> TYPE: DNA
<213> ORGANISM: Artificial Sequence
<220> FEATURE:
<223> OTHER INFORMATION: Description of Artificial Sequence: Primer

<400> SEQUENCE: 7
tttttttttt tttttttca                                              18

<210> SEQ ID NO 8
<211> LENGTH: 26
<212> TYPE: DNA
<213> ORGANISM: Artificial Sequence
<220> FEATURE:
<223> OTHER INFORMATION: Description of Artificial Sequence: Nucleic
      Acid Fragment
<221> NAME/KEY: misc_feature
<222> LOCATION: (1)..(14)
<223> OTHER INFORMATION: n representing any nucleotide
<221> NAME/KEY: misc_feature
<222> LOCATION: (23)..(26)
<223> OTHER INFORMATION: n representing any nucleotide

<400> SEQUENCE: 8
nnnnnnnnnn nnnngatcat ccnnnn                                      26

<210> SEQ ID NO 9
<211> LENGTH: 24
<212> TYPE: DNA
<213> ORGANISM: Artificial Sequence
<220> FEATURE:
<223> OTHER INFORMATION: Description of Artificial Sequence: Depicted
      cDNA
<221> NAME/KEY: misc_feature
<222> LOCATION: (1)..(10)
<223> OTHER INFORMATION: n representing any nucleotide
<221> NAME/KEY: misc_feature
<222> LOCATION: (15)..(24)
<223> OTHER INFORMATION: n representing any nucleotide

<400> SEQUENCE: 9
nnnnnnnnnn gatcnnnnnn nnnn                                        24

<210> SEQ ID NO 10
<211> LENGTH: 18
<212> TYPE: DNA
<213> ORGANISM: Artificial Sequence
<220> FEATURE:
<223> OTHER INFORMATION: Description of Artificial Sequence: Nucleic
      Acid Fragment
<221> NAME/KEY: misc_feature
<222> LOCATION: (9)..(18)
<223> OTHER INFORMATION: n representing any nucleotide

<400> SEQUENCE: 10
ggatgatcnn nnnnnnnn                                               18
```